United States Patent [19]

Mason et al.

[11] Patent Number: 5,397,562
[45] Date of Patent: Mar. 14, 1995

[54] USE OF $^{19}$F MAGNETIC RESONANCE TO NON-INVASIVELY ASSESS PO$_2$ AND TEMPERATURE IN VIVO

[75] Inventors: Ralph P. Mason, Irving; Peter P. Antich, Richardson, both of Tex.

[73] Assignee: Board of Regents, The University of Texas System, Austin, Tex.

[21] Appl. No.: 92,122

[22] Filed: Jul. 15, 1993

Related U.S. Application Data

[63] Continuation-in-part of Ser. No. 482,879, Feb. 21, 1990, Pat. No. 5,236,694.

[51] Int. Cl.$^6$ ............................................. A61B 5/055
[52] U.S. Cl. ...................................... 424/9; 436/173; 128/653.4; 514/832
[58] Field of Search ........................... 424/9; 436/173; 128/653.4, 654; 514/832

[56] References Cited

U.S. PATENT DOCUMENTS

| | | | |
|---|---|---|---|
| 4,558,279 | 12/1985 | Ackerman et al. | 324/315 |
| 4,586,511 | 5/1986 | Clark, Jr. | 128/653 |
| 4,612,185 | 9/1986 | Dean | 424/2 |
| 4,631,190 | 12/1986 | Shen et al. | 424/85 |
| 4,639,364 | 1/1987 | Hoey | 424/9 |
| 4,640,833 | 2/1987 | Tamborski et al. | 424/5 |
| 4,741,900 | 5/1988 | Alvarez et al. | 424/85 |
| 4,838,274 | 6/1989 | Schweighardt et al. | 128/654 |
| 5,068,098 | 11/1991 | Schweighardt et al. | 424/9 |
| 5,080,885 | 1/1992 | Long, Jr. | 424/5 |
| 5,116,599 | 5/1992 | Rogers, Jr. et al. | 424/9 |
| 5,130,119 | 7/1992 | Blaszkiewicz et al. | 424/9 |
| 5,196,348 | 3/1993 | Schweighardt et al. | 436/173 |
| 5,236,694 | 8/1993 | Antich et al. | 424/9 |

FOREIGN PATENT DOCUMENTS 0186947 10/1985 European Pat. Off. .
WO89/02931 4/1989 WIPO .

OTHER PUBLICATIONS

Levy et al, "Synthesis and Characterization of $^{19}$F NMR Chelators for Measurement of Cytosolic Free Ca," Amer. Physiol. Soc., 252:4, pp. C441–C449 (Apr. 1987).

Hamza et al, "Solute–Solvent Interactions in Perfluorocarbon Solutions of Oxygen," J. Am. Chem. Soc. 103:3733–3738 (1981).

Mason et al., "A Novel Editing Technique for $^{19}$F MRI: Molecule–Specific Imaging", Magnetic Resonance Imaging, 8:729–736, (1990).

Jeffrey et al., "Rapid Non-invasive Assessment of Myocardial pO2 Using $^{19}$F NMR Spectroscopy of Sequestered Perfluorocarbon Emulsion", Abstracts of the 63rd Scientific Sessions, III–685, No. 2722; Circulation, 1990, vol. 82, No. 4.

(List continued on next page.)

*Primary Examiner*—Gary E. Hollinden
*Attorney, Agent, or Firm*—Arnold, White & Durkee

[57] ABSTRACT

Oxygen tension of tissue in a living subject may be determined non-invasively by a method which involves: administering to a living mammalian subject a biologically compatible perfluorocarbon emulsion in an amount effective to generate a measurable $^{19}$F spectrum under $^{19}$F NMR spectroscopy; allowing sufficient time to elapse for substantially all of the perfluorocarbon emulsion to be cleared from the vascular system of the subject, with a portion of the perfluorocarbon emulsion becoming sequestered in tissue of the subject; subjecting the tissue in which the perfluorocarbon emulsion has become sequestered to a $^{19}$F magnetic resonance spectroscopy procedure in which simultaneous measurements are made of spin-lattice relaxation rates for at least two separate resonances of the perfluorocarbon emulsion; and comparing the at least two spin-lattice relaxation rates measured in the $^{19}$F magnetic resonance spectroscopy procedure to a predetermined relation of spin-lattice relaxation rate to oxygen tension and temperature for the perfluorocarbon emulsion used, and thereby determining the oxygen tension and temperature of the tissue.

7 Claims, 12 Drawing Sheets

OTHER PUBLICATIONS

Parhami et al., "Fluorine-19 Relaxation Study of Perfluoro Chemicals as Oxygen Carriers," J. Phys. Chem. 87:1928–1938 (1983).

Mason et al., Abstract, "A Non-Invasive Assessment of Myocardial Oxygen Tension," Society of Magnetic Resonance in Medicine, Ninth Annual Meeting (Aug. 18–24, 1990).

Mason et al., "Tissue Oxygenation: A Novel Determination Using $^{19}$F Surface Coil NMR Spectroscopy of Sequestered Perfluorocarbon Emulsion," Magnetic Resonance in Medicine, 18:71–79 (1991).

Berkowitz, "Quantitative Determination of the Partial Oxygen Pressure in the Vitrectomized Rabbit Eye in Vivo Using $^{19}$F NMR," Magnetic Resonance Medicine, 21:233–241 (1991).

Mason et al., Abstract, "Simultaneous Oxygen Tension and Temperature Measurements: A Novel Non-Invasive Technique," 9th International Congress of Radiation Research (1991).

Mason et al., "A Noninvasive Assessment of Myocardial Oxygen Tension: $^{19}$F NMR Spectroscopy of Sequested Perfluorocarbon Emulsion," Magnetic Resonance in Medicine, 27:310–317 (1992).

Wilson et al., "Oxygen Kinetics in Preretinal Perfluorotributylamine," Exp. Eye Res., 5:119–126 (1992).

Berkowitz et al., "Perfluorocarbon Temperature Measurements Using $^{19}$F NMR," NMR in Biomedicine, 5:65–68 (1992).

Mason et al., "Oxygent TM : A Novel Probe of Tissue Oxygen Tension," Biomat., Art. Cells & Immob Biotech., 20 (2–4), pp. 929–932 (1992).

Shukla et al., "The Relationship of Oxygen Tension and Myocardial Mechanical Function: a $^{19}$F NMR Study," Abstracts from the 65th Scientific Sessions, American Heart Association, I-693, No. 2757; Oct. 1992, vol. 86, No. 4.

Mason et al., "A Novel Approach to Localized Oxygen Measurements in Tumours: $^{19}$F NMR of Sequestered Perfluorocarbon," 17th LH Gray Conference, Canterbury, England, Apr. 1992.

Riess, "Overview of Progress in the Fluorocarbon Approach to in vivo Oxygen Delivery," Biomat., Art. Cells & Immob. Biotech., 20 (2–4), pp. 183–202 (1992).

Mason et al, "In Vivo Oxygen Tension and Temperature: Simultaneous Determination Using $^{19}$F NMR Spectroscopy of Perfluorocarbon," Magnetic Resonance in Medicine, 29:296–302 (1993).

Mason et al, "Tumor Oxygen Tension Gradients: New Evidence From $^{19}$F MRI of Perfluorocarbons," Abstract of Papers for the 41st Annual Meeting of Radiation Research Society and the 13th Annual Meeting of the North American Hyperthermia Society, Dallas, Tex., (Mar. 20–25, 1993).

Shukla et al, "Tumor Oxygen Tension: A Comparison of Perfluorocarbon $^{19}$F NMR Probes," Abstract of Papers for the 41st Annual Meeting of the Radiation Research Society and the 13th Annual Meeting of the North American Hyperthermia Society, Dallas, Tex., (Mar. 20–25, 1993).

Mason et al, "Tumor Oxygen Tension: Measurement Using Oxygent TM as a $^{19}$F NMR Probe at 4.7 T," Program and Abstracts for the 5th International Symposium on Blood Substitutes, San Diego, Calif. (Mar. 17–20, 1993).

Hees et al, "Assessment of Changes in Murine Tumor Oxygenation in Response to Nicotinamide Using $^{19}$F NMR Relaxometry of a Perfluorocarbon Emulsion," Magnetic Resonance in Medicine, 29:303–310 (1993).

"Flusol-DA 20%," Investigator's Brochure (Jun. 6, 1986).

Alliance Pharmaceutical Corp., "Publication Information" (Sep. 30, 1992).

Taylor et al, "$^{19}$F-Nuclear Magnetic Resonance: Measurements of [O$_2$] and pH in Biological Systems," Biophys. Journal, 53:227–233 (Feb., 1988).

Fishman et al., "Oxygen-Sensitive $^{19}$F NMR Imaging of the Vascular System In Vivo," Magnetic Resonance Imaging, 5:279–285 (1987).

Babcock et al, "Effect of Homonuclear J Modulation on $^{19}$F Spin-Echo Images," Magnetic Resonance in Medicine 17:179–188 (1991).

Mason et al, "A Novel Editing Technique for $^{19}$F MRI: Molecule-Specific Imaging," Magnetic Resonance Imaging 8:729–736 (1990).

Mason et al., "Perfluorocarbon Imaging In Vivo: A $^{19}$F MRI Study in Tumor-Bearing Mice," Magnetic Resonance Imaging 7:475–485 (1989).

Mason et al., "Fluorinated Polymeric Molecular Probes for Non-Invasive Assessment of pH by Magnetic Resonance Spectroscopy," Abstract form, The Society of Nuclear Medicine 39th Annual Meeting, Los Angeles, Calif. (Jun. 9–12, 1992).

(List continued on next page.)

OTHER PUBLICATIONS

Mehta et al., "Novel Fluorinated Polymeric Molecular Probes for F-19 Magnetic Resonance Imaging: Syntheses & Characterization of Fluorinated Biopolymers," Abstract Pap. Am. Chem. Soc., 202:102 (1991).

Mason et al., "In Vivo Oxygen Tension and Temperature: Stimulaneous Determination Using $^{19}$F NMR Spectroscopy of Perfluorocarbon," 1991, Society of Magnetic Resonance in Medicine.

Mehta et al, "New $^{19}$F Magnetic Resonance Imaging Agents for Drug Targeting," Proceedings of the 38th Annual Meeting 32:5, No. 731 (May, 1991).

Derwent Abstract No. 73-33347u (Meito Sangyo Company, Ltd.) (1973).

Miura et al, "8-Fluoro-8-Demethylriboflavin as a $^{19}$F-Probe for Flavin-Protein Interaction. A $^{19}$F NMR Study With Egg Whit Riboflavin Binding Protein," Biochemical and Biophysical Research Communications, 110:2, pp. 406–411 (Jan. 27, 1983).

Ratner et al, "$^{19}$F Magnetic Resonance Imaging of the Reticuloendothelial System," Magnetic Resonance in Medicine, 5:548–554 (1987).

Ratner et al, "Detection of Tumors with $^{19}$F Magnetic Resonance Imaging," Invest. Radiol., 23:361–364 (1988).

Taylor et al, "Fluorinated α-Methylamino Acids as $^{19}$F NMR Indicators of Intracellular pH," Biophys. Journal, 43:261–267 (Sep. 1983).

Deutsch et al, "Intracellular pH as Measured by $^{19}$F NMR$^a$," Annals New York Academy of Sciences, 508:33–47 (1987).

Metcalfe et al, "Free Cytosolic Ca$^{2+}$ Measurements with Fluorine Labelled Indicators Using $^{19}$FNMR," Cell Calcium, 6:183–195 (1985).

Smith et al, "Design of an Indicator of Intracellular Free Na$^+$ Concentration Using $^{19}$F-NMR," Biochimica et Biophysica Acta, 889:72–73 (1986).

Evers et al, "The Potency of Fluorinated Ether Anesthetics Correlates With Their $^{19}$F Spin-Spin Relaxation Time in Brain Tissue," Biochemical and Biophysical Research Communications, 151:3, pp. 1039–1045 (Mar. 30, 1988).

Hull et al, "Chain-Fluorinated Polyamines as Tumour Markers," NMR in Biomedicine, 1:1, pp. 11–19 (1988).

Shimizu et al, "Tumor Imaging with Anti-CEA Antibody Labeled $^{19}$F Emulsion," Magnetic Resonance in Medicine, 5:290–295 (1987).

Levy et al, "The Trifluoroacetylation of Insulin," Biochimica et Biophysica Acta, 310:398–405 (1973).

Wolfrom et al, "Trifluoroacetyl as an N-Protective Group in the Synthesis of Purine Nucleosides of 2-Amino-2-Deoxy Saccharides," Carbohyd. Res., 11:63–76 (1969).

Goldberger et al, "The Reversible Masking of Amino Groups in Ribonuclease and Its Possible Usefulness in the Synthesis of the Protein," Biochemistry, 1:3, pp. 401–405 (May, 1962).

Brauer et al., "$^{19}$F Nuclear Magnetic Resonance Studies of Selectively Fluorinated Derivatives of G- and F-Actin," Biochemistry, 25:2187–2191 (1986).

Capon et al, "Fluorine-19 Magnetic Resonance Spectroscopic Investigation of the Binding of 2-deoxy-2-trifluoroacetamido-.alpha.-D-glucose to Lysozyme," Chemical Abstracts, 75(11):77211a (1971).

Hall et al, "NMR Study of the Effects of Fluorine Substituents on the Association Between Lysozyme and Derivatives of 2-amino-2-deoxy-D-Glucose," Chemical Abstracts, 78(7):39873x (1972).

Moussebois et al, "Separation of N-.alpha.-trifluoroacetyl-DL-lysine from Potassium Trifluoroacetate by Liquid Chromatograph," Chemical Abstracts, 77(15):102186x (1972).

Kricheldorf et al, "Preparation of N-trifluoroacetylamino Acids and Their Trimethylsilyl Esters," Chemical Abstracts, 81(15):91911j (1974).

Douy et al, "Amphipathic Block Copolymers with Two Polypeptide Blocks: Synthesis and Structural Study of Poly(n.epsilon.-trifluoroacetyl-L-Lysine)-Polysarcosine Copolymers," Chemical Abstracts, 107(5):40320p (1987).

Kol'tsova et al, "Dextran Derivatives. IV. Dextran Acylation by Imidozolides of N-protonated Amino Acids," Chemical Abstracts, 78(1):4443e (1972).

Schallenberg et al., "Ethyl Thioltrifluoroacetate as an Acetylating Agent with Particular Reference to Peptide Synthesis," Journal of American Chemical Society, 777:2779–2783 (1955).

"Modified Antibody for NMR Diagnostic Method—Comprises Reactive Antibody Modified with Flourine cpd," Derwent Abstract, No. 88-195824 (Asahi Kasei Kogyo, 7 Jun. 1988).

40 SECS

40 SECS

USE OF ¹⁹F MAGNETIC RESONANCE TO NON-INVASIVELY ASSESS PO₂ AND TEMPERATURE IN VIVO

This is a continuation-in-part of application Ser. No. 482,879, filed on Feb. 21, 1990, now U.S. Pat. No. 5,236,694. That application is incorporated here by reference.

BACKGROUND OF THE INVENTION

Nuclear magnetic resonance (NMR) techniques are finding increasing use in medical applications. NMR imaging, or magnetic resonance imaging (MRI) as it is sometimes known, has been found to be useful in the detection of a variety of diseases and disorders. MRI has several advantages over other imaging techniques. For example, unlike computerized tomographic methods, MRI does not employ ionizing radiation, and therefore is believed to be safer. Also, MRI can provide more information about soft tissue than can some other imaging methods.

The majority of the NMR techniques developed so far have been based on imaging of hydrogen nuclei. However, other nuclei offer potential advantages with respect to NMR. ¹⁹F in particular is of interest. The fluorine nucleus offers a strong NMR signal magnitude (high gyromagnetic ratio) close to that of protons. Virtually no imagable fluorine exists naturally in the human body, so essentially no background signal exists; any detectable signal comes only from whatever ¹⁹F has been administered to the subject.

¹⁹F is a stable isotope and is naturally abundant, so there is no need for isotopic enrichment. Because its gyromagnetic ratio is about 94% that of hydrogen, existing equipment designed to image protons can be inexpensively adapted for ¹⁹F.

One important physiological parameter which might be assessed by means of ¹⁹F NMR is tissue oxygen tension ($pO_2$). Oxygen is required for efficient function by most tissues; hypoxia leads to rapid cellular dysfunction and damage. In addition, tumor cells exhibit regional hypoxia, and their response to therapy is strongly dependent on the degree and extent of hypoxia. Tumors with very low $pO_2$ exhibit marked resistance to radiotherapy. Many chemotherapeutic agents act preferentially on euoxic or hypoxic tissue. Thus, a reliable method of estimating tumor $pO_2$ would be of significant help in treatment optimization for individual cancer patients.

Traditional techniques of measuring oxygen tension in tissue are generally invasive and sample localized volumes only, e.g., oxygen microelectrodes, mass spectrometer probes, or biopsy and cryospectrophotometry. Some noninvasive techniques which are available examine superficial tissues only, e.g. surface electrodes or fluorescence. Thus, the existing methods of measuring $pO_2$ have significant problems and limitations.

The ¹⁹F NMR spin-lattice relaxation rate ($R_1 = 1/T_1$) of perfluorocarbon emulsions is sensitive to oxygen tension. Therefore, ¹⁹F MRI has been used to map tissue $pO_2$, but the data acquisition is slow (e.g., hours), in organs or tissue with low PFC concentrations, such as heart, brain, and tumor, and further tends to exhibit poor signal to noise ratios. ¹⁹F MRI requires specific observation of a single resonance, or the application of elaborate deconvolution, and thus only a single estimate of $pO_2$ may be obtained.

Thus, a need exists for improved methods of measuring tissue oxygen tension. A non-invasive method that could measure $pO_2$ in vivo accurately and rapidly could be significant in understanding the mechanisms of tissue function, and in planning and managing cancer therapy.

SUMMARY OF THE INVENTION

The present invention relates to a method of noninvasively determining oxygen tension of tissue in a living subject. The method involves first administering to a living mammalian subject a biologically compatible ¹⁹F-containing spectroscopy agent in an amount effective to generate a measurable ¹⁹F spectrum under ¹⁹F NMR spectroscopy. Sufficient time is allowed to elapse for substantially all of the ¹⁹F-containing spectroscopy agent to be cleared from the vascular system of the subject (e.g., ≧95% cleared, and preferably 100% cleared), with a portion (preferably more than 50%) of the ¹⁹F-containing spectroscopy agent becoming sequestered in tissue of the subject. (Often at least 95% of the agent will become sequestered in the liver and spleen.) Tissue in which the ¹⁹F-containing spectroscopy agent has become sequestered is subjected to a ¹⁹F magnetic resonance spectroscopy procedure, in which at least two independent measurements of spin-lattice relaxation rates are made. In this context, independent measurements are defined as spin-lattice relaxation rates from at least two separate resonances of the ¹⁹F-containing spectroscopy agent, which can be measured simultaneously. Finally, at least two spin-lattice relaxation rates measured in the ¹⁹F magnetic resonance spectroscopy procedure are compared to a predetermined relation of spin-lattice relaxation rate to oxygen tension at a given temperature and magnetic field for the ¹⁹F-containing spectroscopy agent used, and thereby the oxygen tension and optionally also the temperature of the tissue are determined. This comparison can be done graphically, or by solving simultaneous equations determined from the predetermined relationship.

If at least two measurements of spin-lattice relaxation rates are made at different times, the dynamic change in oxygen tension can be determined therefrom.

In a preferred embodiment of the present invention, the method includes the steps of:

administering to a living mammalian subject a biologically compatible perfluorocarbon emulsion in an amount effective to generate a measurable ¹⁹F spectrum under ¹⁹F NMR spectroscopy;

allowing sufficient time to elapse for substantially all of the perfluorocarbon emulsion to be cleared from the vascular system of the subject, with a portion of the perfluorocarbon emulsion becoming sequestered in tissue of the subject;

subjecting tissue in which the perfluorocarbon emulsion has become sequestered to a ¹⁹F magnetic resonance spectroscopy procedure in which simultaneous measurements are made of spin-lattice relaxation rates for at least two separate resonances of the perfluorocarbon emulsion; and comparing the at least two spin-lattice relaxation rates measured in the ¹⁹F magnetic resonance spectroscopy procedure to a predetermined relation of spin-lattice relaxation rate to oxygen tension and temperature for the perfluorocarbon emulsion used, and thereby determining the oxygen tension and temperature of the tissue.

In another embodiment of the present invention, two tissue regions are assessed simultaneously based on the discrete distributions of two separate perfluorocarbons, each of which has a distinct spectrum.

The present invention uses $^{19}F$ NMR spectroscopy to measure the $^{19}F$ NMR spin-lattice relaxation rate ($R_1$) of agents such as perfluorocarbon emulsions that are sequestered in tissue. Spectroscopy has the advantage of providing a multi-resonance spectrum. NMR spectroscopy also offers superior sensitivity and thus considerably improved temporal resolution over $^{19}F$ MRI, albeit with a loss of spatial resolution. This improved temporal resolution permits observation of dynamic changes in $pO_2$, even in organs that take up as little PFC as the heart. Pulse-burst saturation recovery spectroscopy is an especially preferred technique, providing rapid determinations of $pO_2$.

The $R_1$ of each resonance is sensitive not only to $pO_2$, but also to temperature and magnetic field. Thus, calibration curves are required at the specific field of investigation. Separate calibration curves are required for $pO_2$ at different temperatures.

Because each resonance is within a single molecule, each nucleus will be at the same temperature and $pO_2$. Thus, the $pO_2$ estimated from each of the two $R_1$s will only concur when the temperature estimate is also correct. This is significant since there are often considerable differences between temperatures at different sites in an animal, e.g., core rectal temperatures versus skin temperatures, and these may vary during the course of a study. The simultaneous observation of a pair of $^{19}F$ resonances provides an internal control to validate the $pO_2$ estimates.

Another embodiment of the present invention relates to the finding that $pO_2$ and temperature are uniquely and simultaneously defined by the relaxation rates of a pair of resonances. In other words, for a particular magnetic field, for each combination of a particular $^{19}F$-containing agent, temperature, and $pO_2$, there is a unique $R_1$ calibration curve. Therefore, if one measures more than one resonance for a given tissue with a $^{19}F$-containing agent present in that tissue, the plurality of readings can be compared to pre-existing $R_1$ calibration curves, and the $pO_2$ and temperature of the subject tissue can be determined simultaneously without having to directly measure either. This eliminates the need to make estimates of tissue temperature by other means which may not be reliable, especially for tissue relatively far from the body's surface.

Flow of PFC through tissue produces artifacts in the measurement of $T_1$. The problems caused by flow when using $^{19}F$-containing material circulating in the vascular system are avoided in the present invention by allowing substantially complete vascular clearance of the perfluorocarbon prior to examination, and then observing the perfluorocarbons sequestered in tissue.

The advantages of the present invention include high sensitivity to $pO_2$, ability to determine $pO_2$ and temperature simultaneously, corroborative measurement from multiple resonances, and thus improved accuracy, ability to assess tissues far from the body's surface, ability to assess localized $pO_2$ on the basis of discrete distribution of perfluorochemical in the tissue, and the ability to measure dynamic changes in $pO_2$.

The present invention can be used to determine $pO_2$ in a variety of organs and tissues, including liver, spleen, heart, and tumor. It should have a number of useful applications in medicine, such as assessing regions of hypoxia in solid tumors for use in planning and managing radio- and chemotherapy; assessing perfusion in ischemic heart, brain, kidney, and other tissue; and determining temperature field distributions during hyperthermia.

BRIEF DESCRIPTION OF THE DRAWINGS

FIG. 5 shows the influence of carbogen breathing on tissue oxygenation.

DETAILED DESCRIPTION OF SPECIFIC EMBODIMENTS

Figure 1:
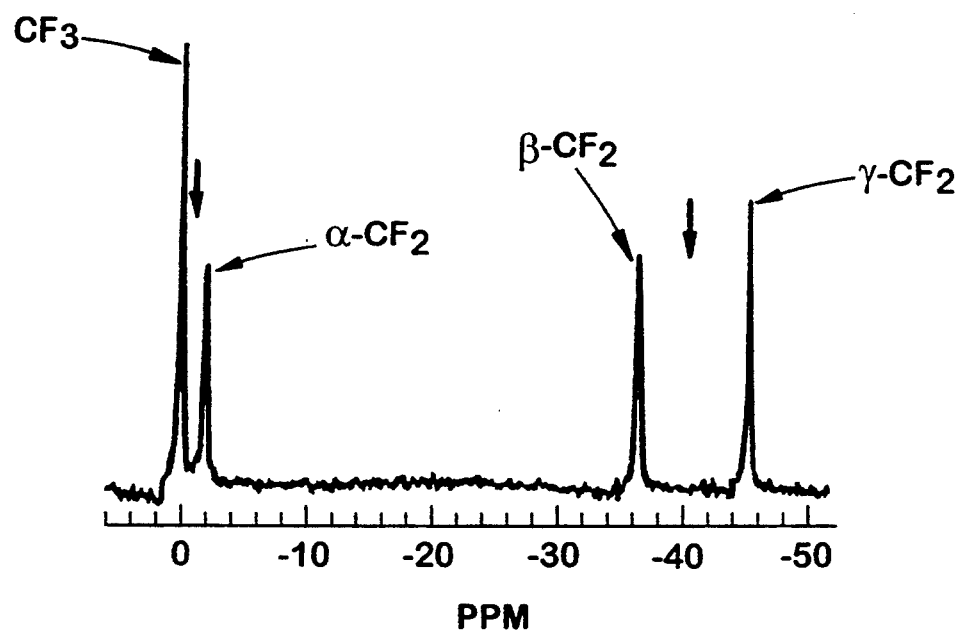
FIG. 1 shows a $^{19}F$ NMR spectrum of the perfluorocarbon (PFC) emulsion Oxypherol-ET.

The present invention involves the use of biologically-compatible $^{19}$F-containing compositions, which can be administered to a living mammalian subject without causing undue adverse consequences for the subject, such as toxicity. One particular group of compositions which are useful in the present invention is perfluorocarbon (PFC) emulsions, such as those that have been tested as potential blood substitutes.

Perfluorocarbons are essentially insert and exhibit very high gas solubility. They are immiscible with water, but may be formulated as emulsions (i.e., a dispersion of small droplets in an aqueous phase) with pluronic or egg yolk phospholipids. The pH and osmotic pressure of the emulsions are preferably adjusted to physiologic values.

Suitable perfluorocarbon emulsions include Oxypherol (FC-43 Emulsion; perfluorotributylamine 25% w/v, polyoxypropylene-polyoxyethylene copolymer 3.2% w.v, in distilled water, Alpha Therapeutics Corp., Los Angeles, Calif., and Green Cross Corp., Osaka, Japan), Oxygent (perflubron (perfluorooctyl bromide) emulsion, Alliance Pharmaceutical Corp., San Diego, Calif.), Fluosol (perfluorodecalin and perfluorotripropylamine in 7:3 ratio, stabilized by Pluronic F-68 and phospholipids, Green Cross Corp.), and Therox (F-44E, trans-1,2 bis(perfluorobutyl)-ethylene emulsion, DuPont, Deepwater, N.J.).

Other compounds which can be used include perfluorooctyl iodide, hexafluorobenzene, perfluorodimethyl cyclohexane, and tris(trifluoromethyl)-benzene. It is also believed that perfluorooctyl chloride and compounds with 1,8 dihalooctane structures would be useful in the present invention.

PFC emulsions, when administered to a living subject, will be cleared from the vasculature in a matter of a few hours or a few days. A portion of the administered PFC will become sequestered in tissue in the subject, and will remain there long after the PFC is cleared from the bloodstream (i.e., for days to years). For example, perflubron has a half-life of $\approx 3$ days in the major organs versus 65 days for the perfluorotripropylamine component of Fluosol.

In this context it should be noted that dilution of a perfluorocarbon and emulsification have been shown to have no significant effect on T$_1$. Also R$_1$ is unaffected by changes in pH, common proteins, or blood, or the presence of paramagnetic ions.

Each PFC emulsion has a unique multi-resonant spectrum, which is characterized by absolute ($\delta$) and relative ($\Delta\delta$) chemical shifts, relative signal intensities, and spin-lattice (R$_1$=1/T$_1$) and spin-spin (R$_2$=1/T$_2$) relaxation rates. Each of these parameters can be exploited in using PFC's to probe tissue physiology. The PFC of choice depends on characteristic NMR properties together with the usual considerations of emulsion stability, vascular retention, tissue targetability, and ultimate clearance from the body.

It is presently believed that Oxygent is considerably more sensitive to changes in pO$_2$ than many other commercial PFC emulsions, such as Oxypherol and Fluosol. In addition, the long transverse relaxation time T$_2$ of Oxygent makes it particularly useful for MR. Each of the three above-listed emulsions have shown similar clearance characteristics from the vasculature, and similar uptake and biodistribution in tissues. Oxygent, however, is eliminated much more rapidly from the body. Neat PFC's, such as hexafluorobenzene have shown even greater sensitivity to changes in pO$_2$, but the biological compatibility of these materials is not certain.

The present invention can make use of $^{19}$F NMR equipment that is known to those skilled in this field (e.g., GE (Bruker) CSI Omega 4.7 T/40 cm spectrometer, Bruker AM 500 FT, or Siemens Magnetom H 1.5).

EXAMPLE 1

Three distinct types of experiments with a $^{19}$F-containing emulsion were performed: calibration, measurements in vivo, and measurements in excised tissues. All NMR experiments were performed using a Nicolet NT300 (7 Tesla) spectrometer. The perfluorocarbon emulsion Oxypherol-ET (Alpha Therapeutics Corp. Los Angeles, Calif.) was prepared according to the manufacturer's instructions.

Standard gases were bubbled through aliquots of the emulsion in order to obtain specific oxygen concentrations: (i) 95% O$_2$, 5% CO$_2$ (carbogen), (ii) 12.2% O$_2$, 87.8% N$_2$, (iii) 8% O$_2$, 92% N$_2$, and (iv) 100% N$_2$. An additional sample was prepared by adding sodium dithionite (18 mg, Aldrich, St. Louis, Mo.) to Oxypherol-ET emulsion (2.5 ml), giving 0% O$_2$. (An approximate conversion of 760 Torr=100% may be used.)

The standard samples were placed in gas-tight NMR tubes (Wilmad Taperlok 528SJH, Buena, N.J.). Calibration experiments were performed using a high-resolution 5 mm Bruker fluorine probe at 34.2° C. with temperature regulation using an FTS TC 44 variable temperature unit (Stone Ridge, N.Y.), together with the Nicolet variable temperature unit incorporated in the NMR system. The probe was allowed to equilibrate for about 1½ hour at this temperature until a stable value was observed (>½ hour) in a sample of Oxypherol-ET in the probe using a thermocouple (1 mm in length, Sensortek Corp., Clifton, N.J.) and an Omega digital thermometer (Stamford, Conn.). Once equilibrium was achieved, the temperature was found to be stable within ±0.1° C. over ½ hour. Each sample was allowed to equilibrate for more than 10 minutes in the probe, this being adequate to achieve the stable planned temperature prior to NMR observation. Shimming was performed on the $^{19}$F signal at 282.31 MHz.

T$_1$ experiments were performed at 282.31 MHz on the downfield CF$_3$ plus CF$_2$ resonances and on the two upfield CF$_2$ resonances separately with the spectrometer frequency placed midway between the pair of resonances in each case, as shown in FIG. 1. A pulse-burst saturation recovery experiment was performed using 20 saturating pulses (14 µs) followed by an incremental delay (25 values ranging from 5 ms to 15 s) and a 14 µs pulse and acquisition. Four transients were acquired at each delay using phase cycling and quadrature detection, with 1K real and imaginary data points across a spectral width of ±770 Hz for the downfield resonances and ±1900 Hz for the upfield resonances, with the total spectral width being ±8196 Hz. A 10 Hz exponential line broadening was applied prior to Fourier transformation and the $T_1$ spin-lattice relaxation time was estimated using the formula $$I = a + b \exp(-\tau/T_1)$$

where I is the signal intensity, $\tau$ is the variable recovery time after saturation, and a and b are constants. (More recently it has been found that the more general equation $$I = a*(1-(b+1)* \exp(-\tau/T_1))$$

gives a better estimate of $T_1$.) Data were processed using regression analysis software (NMR Inc., Syracuse, N.Y.). $T_1$ experiments were performed on three separate occasions, using fresh emulsion aliquots, to test the reproducibility of the technique.

Fresh Oxypherol-ET emulsion (1 ml, a dose of $\approx 40$ ml/kg) was administered iv on three consecutive days to each of three Meth-A tumor-bearing BALB/C mice. (Oxypherol-ET is not toxic at this dose.) The perfluorocarbon was allowed to clear from the vasculature over a period of at least 6 days, and this clearance was verified by examining a sample of blood by high-resolution $^{19}F$ NMR. Each mouse was anesthetized with Nembutal (Abbott Laboratories, Chicago, Ill.; 50 mg/kg ip) and placed in a home-built probe with the tumor against a 1.8 cm diameter single-turn surface coil tuned to 282.31 MHz. The mouse was held in place by Velcro straps and warm water circulating coils passed around the lower abdomen. The mouse core body temperature was monitored using a rectally inserted thermocouple connected to a digital thermometer outside the magnet. (It has subsequently been found that optical fiber probes provide better temperature monitoring; thermocouples tend to act as antennae introducing noise to the spectrum.) The mouse temperature was maintained at $34.0 \pm 1.5°$ C. The $T_1$'s of the perfluorocarbon resonances were estimated, as before, using a saturation recovery sequence. This probe required a longer pulse width (80 μs) and eight transients were acquired at each time interval. Each $T_1$ measurement required 6 min. and the $T_1$ experiments were repeated to demonstrate reproducibility and to examine changes occurring when the mice breathed carbogen. In order to observe the liver, the surface coil was placed against the chest of the mouse.

Following the in vivo experiments, a mouse was sacrificed and the major organs were dissected. Samples of liver and tumor ($\approx 100$ mg) were suspended in $D_2O$ in 5 mm NMR tubes and saturation recovery $T_1$ experiments were performed at $34.2°$ C., as for the calibration experiment.

Figure 2:
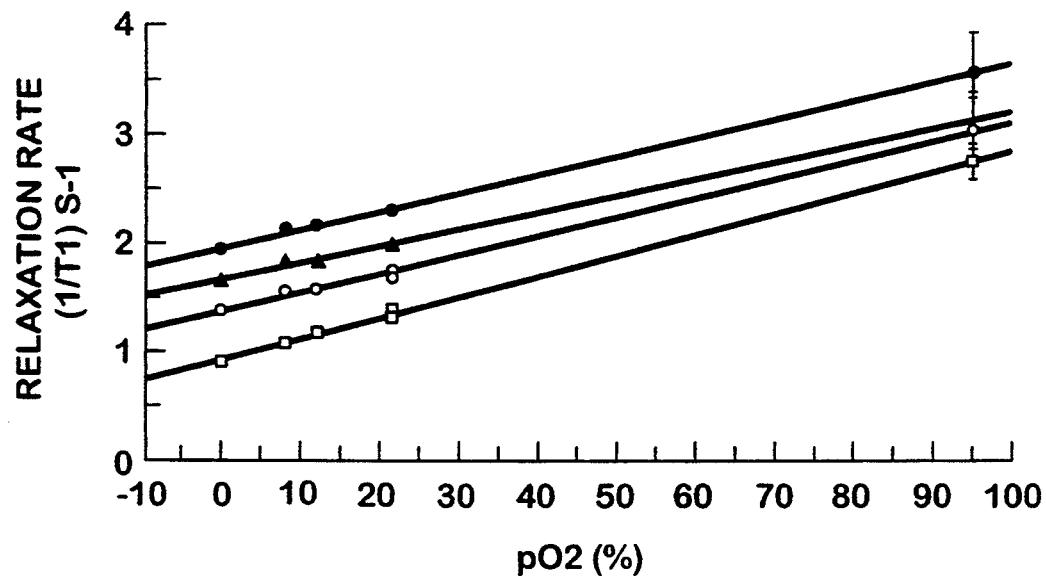
FIG. 2 the variation of spin-lattice relaxation rate with oxygen tension for Oxypherol.

The calibration results show that Oxypherol-ET has four $^{19}F$ resonances, which are well resolved at 282.31 MHz, as shown in FIG. 1. The arrows in FIG. 1 indicate the positions of the spectrometer frequency for the separate $T_1$ experiments. FIG. 2 shows the correlation of spin-lattice relaxation rate ($1/T_1$) relative to oxygen tension ($pO_2$) for each of the four resonances ($CF_3$ □, $\alpha$-$CF_2$ ●, $\beta$-$CF_2$ ▲ and $\gamma$-$CF_2$ ○) at $34.2°$ C. (It is preferable to refer to resonances by chemical shift rather than by name as the literature contains contradictions. Ultimately, it is crucial that the correct calibration is applied to a given resonance.) The values at 0 and 95% $pO_2$ represent the means of three individual determinations, while the other points are individual values. Error bars indicate standard errors of the mean; for low $pO_2$ the error bars are smaller than the symbols.

There is clear linearity in each case ($1/T_1 \propto pO_2$). The relationships are described in Table 1.

TABLE 1

| | Dependence of Spin-Lattice Relaxation Rate ($1/T_1$) on Oxygen Tension | |
|---|---|---|
| $CF_3$ | $1/T_1 = 1.95 \times 10^{-2}$ (% $pO_2$) + 0.92 | r > 0.998 |
| $\alpha$-$CF_2$ | $1/T_1 = 1.69 \times 10^{-2}$ (% $pO_2$) + 1.94 | r > 0.999 |
| $\beta$-$CF_2$ | $1/T_1 = 1.59 \times 10^{-2}$ (% $pO_2$) + 1.68 | r > 0.998 |
| $\gamma$-$CF_2$ | $1/T_1 = 1.82 \times 10^{-2}$ (% $pO_2$) + 1.39 | r > 0.997 |

The spin-lattice relaxation rate ($1/T_1$) of the $CF_3$ group was found to range from $0.920 \pm 0.008$ s$^{-1}$ ($pO_2 = 0\%$) to $2.78 \pm 0.19$ s$^{-1}$ ($pO_2 = 95\%$) at $34.2°$ C. The spin-lattice relaxation time ($T_1$) of the $CF_3$ group ranged from 1086 to 360 ms, while the $\alpha$-$CF_2$ resonance had the shortest $T_1$ values, ranging from 515 to 282 ms over the same range ($pO_2 = 0$ to 95%).

Figure 3:
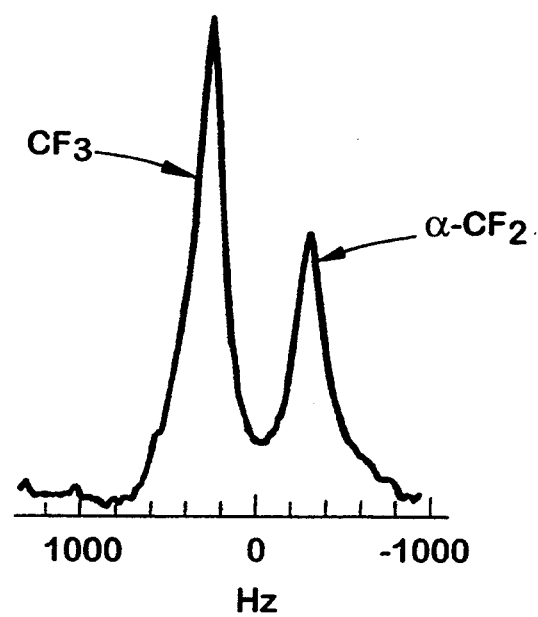
FIG. 3 shows a $^{19}F$ spectrum of the downfield $CF_3$ and $CF_2$ resonances of Oxypherol measured in vivo from a mouse tumor.

FIG. 3 shows the well-resolved downfield resonances in a typical 282 MHz $^{19}F$ spectrum obtained from a mouse tumor in vivo with the surface coil. The 2K real and imaginary data points were acquired across a spectral width of $\pm 2.5$ kHz and the spectrum is the average of eight transients. A 20 Hz exponential line broadening was applied prior ro Fourier transformation.

Figure 4:
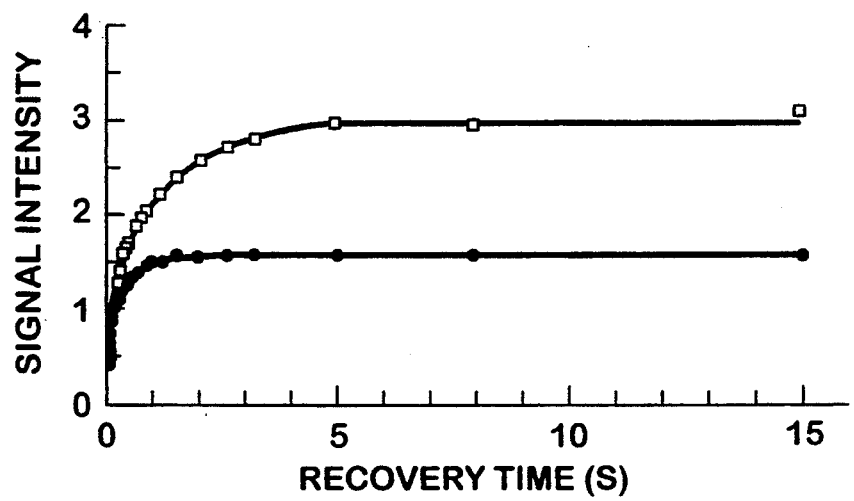
FIG. 4 shows relaxation curves for the $CF_3$ and $CF_2$ resonances of Oxypherol observed from a mouse tumor in vivo.

FIG. 4 shows the relaxation curves for the $CF_3$ (□) and $\alpha$-$CF_2$ ● resonances in a typical experiment from a Meth-A tumor in vivo using the surface coil. The points were obtained from a series of spectra and the curves fit the formula $$I = a + b \exp(-\tau/T_1)$$

The signal to noise ratio (S/N) ranged from 7 to 70, and $T_1$ values of $1086 \pm 28$ and $533 \pm 18$ ms were determined for the $CF_3$ and $\alpha$-$CF_2$ resonances, respectively. By reference to FIG. 2, these $T_1$ values give estimated values of $pO_2 = 0.0 \pm 2.5\%$ ($CF_3$) and $-3.8 \pm 3.4\%$ ($CF_2$), respectively. Clearly, $pO_2$ cannot be negative. The $\alpha$-$CF_2$ result may be interpreted as giving an upper limit of $pO_2 < 3.0\%$, at the 95% confidence level, in excellent agreement with the value obtained from the more sensitive $CF_3$ resonance.

For a group of three Meth-A tumors ranging in size from 1.1 to 8.0 cm$^3$ the mean $pO_2$ was found to be $0.7 \pm 2.5\%$. This result was obtained as the sample average of the $CF_3$ resonance, $0.0 \pm 1.5\%$, and of the $\alpha$-$CF_2$, $1.3 \pm 3.5\%$. These measurements were repeatable: a second series of measurements gave essentially identical values with a mean of $pO_2 = 2.0 \pm 2.4\%$.

An anesthetized Meth-A tumor-bearing mouse was exposed to carbogen at a flow rate of five dm$^3$/min to assess the effect on tumor and liver $pO_2$. The surface coil was placed respectively over the tumor or liver of the anesthetized mouse and $^{19}F$ NMR spectra were obtained prior to administration of carbogen and at 5 and 15 min. after the start of carbogen breathing (t=0). See FIG. 5. Individual $T_1$ estimates required 6 min. There are two curves for each organ, representing measurements of $T_1$ for the $CF_3$ (upper) and $\alpha$-$CF_2$ (lower) resonances, respectively.

Figure 5A:
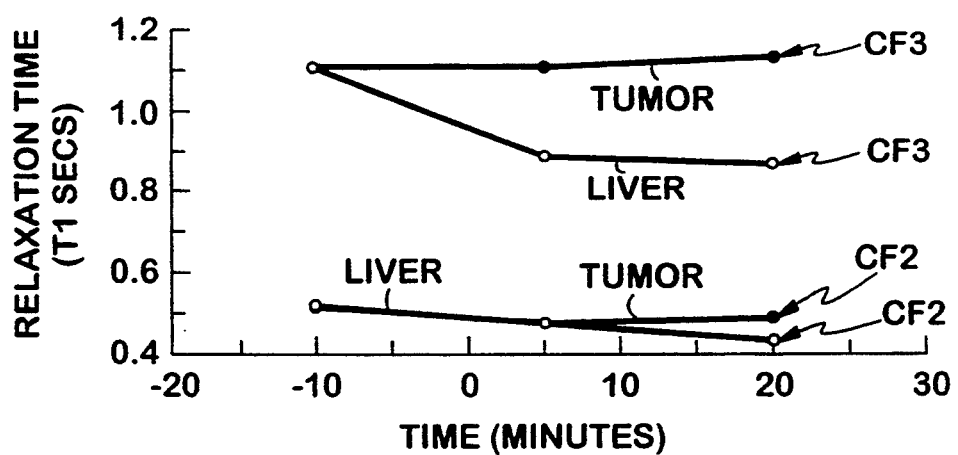
FIG. 5A shows the variation of measured relaxation time.
Figure 5B:
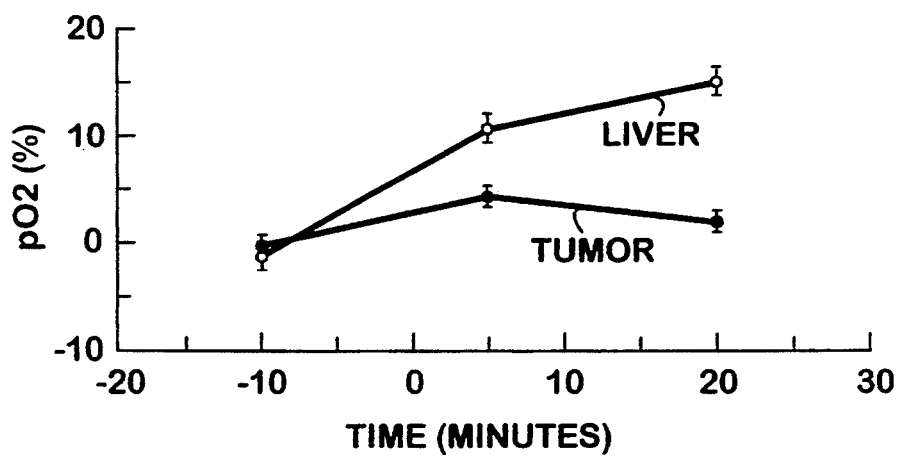
FIG. 5B shows the variation of $pO_2$ determined from the relaxation measurements.

The results showed that when an anesthetized Meth-A tumor-bearing mouse was exposed to carbogen (95% $O_2$, 5% $CO_2$) at a flow rate of 5 dm$^3$/min, there was no significant change in tumor $pO_2$ over a period of 40 min. In contrast, when similar measurements were made with the surface coil placed over the chest, to obtain signal from the liver, the $pO_2$ increased from $-1.0 \pm 3.6\%$ ($pO_2 < 6.2\%$, $p > 0.95$) to $14.6 \pm 3.7\%$ as shown in FIG. 5. It is apparent that the $T_1$ of the signals from the tumor do not vary significantly with breathing oxygen, whereas those from the liver are shortened. FIG. 5B shows the variation of tissue oxygen tension derived from the $T_1$'s in FIG. 5A.

Table 2 shows the consistency of $pO_2$ estimates from each of the resonances of perfluorotributylamine sequestered in the tumor of a living mouse. Estimates obtained from excised tissues are also shown.

TABLE 2

Comparison of $pO_2$ Estimates Obtained from Each of the $^{19}F$ Resonances

|  |  | $CF_3$ | $\alpha$-$CF_2$ | $\beta$-$CF_2$ | $\gamma$-$CF_2$ | $pO_2^a$ |
|---|---|---|---|---|---|---|
| In vivo |  |  |  |  |  |  |
| Tumor | $T_1^b$ | $1039 \pm 23^d$ | $494 \pm 15$ | $581 \pm 32$ | $673 \pm 11$ |  |
|  | $pO_2^c$ | $1.9 \pm 2.2^d$ | $5.1 \pm 3.0$ | $2.6 \pm 3.0$ | $5.3 \pm 1.6$ | $3.7 \pm 1.3$ |
| Excised tissue |  |  |  |  |  |  |
| Liver | $T_1$ | $1164 \pm 20$ | $526 \pm 7$ | $585 \pm 15$ | $766 \pm 5$ |  |
|  | $pO_2$ | $< 1.0**$ | $< 0.5*$ | $0.0 \pm 2.5$ | $< 1.0**$ | $< 1.3*$ |
| Tumor | $T_1$ | $1157 \pm 36$ | $527 \pm 13$ | $609 \pm 12$ | $729 \pm 14$ |  |
|  | $pO_2$ | $< 3.1*$ | $< 2.5*$ | $< 1.6*$ | $< 2.8*$ | $< 1.0**$ |

$^a$Mean oxygen tension estimated from the four resonances.
$^b$Spin-lattice relaxation time (ms).
$^c$Oxygen tension (%).
$^d\pm$ 1 SD.
*Probability $> 0.95$.

The signal to noise ratio of 7 to 70 in these experiments indicates that the number of acquisitions could be reduced to give a more rapid estimate. The low $pO_2$ values determined for tumors are consistent with values previously reported in other animal tumors.

EXAMPLE 2

Calibration experiments similar to those in Example 1 were performed sequentially at different temperatures (27.2° C., 34.2° C., 40.6° C., 35.9° C., and 32.6° C.). Temperature was regulated using an FTS TC 44 variable temperature unit (Stone Ridge, N.Y.), together with the Nicolet variable temperature unit incorporated in the NMR system. The probe was allowed to equilibrate until a stable value was observed ($> \frac{1}{2}$ hour) using a thermocouple (Sensortek Corp., Clifton, N.J.) in a sample of Oxypherol-ET in the probe. Once equilibrium was achieved, the temperature was found to be stable within $\pm 0.1°$ C. over $\frac{1}{2}$ hour. Each sample was allowed to equilibrate for more than 10 minutes in the probe, this being adequate to achieve the stable desired temperature prior to NMR observation.

Spin-lattice relaxation rates at 7 Tesla were determined using a pulse-burst saturation recovery experiment on the downfield $CF_3$ and $CF_2$ resonances with the spectrometer frequency placed midway between the pair of resonances, at 282.31 MHz. 4K data points were acquired across a spectral width of $\pm 8196$ Hz and a 10 Hz exponential line broadening was applied prior to Fourier transformation. $R_1$ was estimated using a three parameter fit. Relaxation experiments were performed on three separate occasions using fresh emulsion aliquots, to test the reproducibility of the technique.

Oxypherol-ET emulsion was administered to Meth-A tumor-bearing BALB/C mice and the perfluorocarbon was allowed to clear from the vasculature over a period of at least 6 days. The mice were sacrificed and the major organs dissected. Samples of liver and tumor ($\approx 100$ mg) were suspended in $D_2O$ and relaxation experiments were performed at the various temperatures.

Figure 6A:
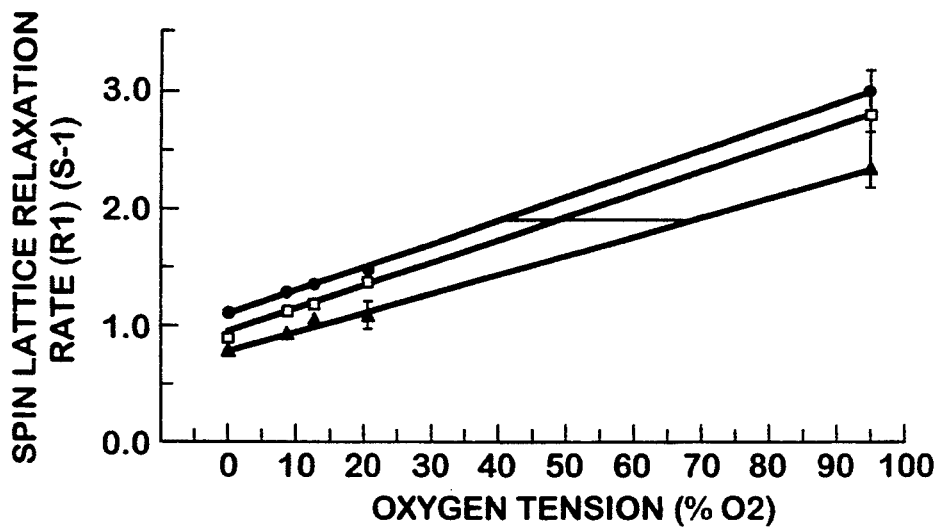
FIG. 6 shows the relation of spin-lattice relaxation rate to $pO_2$ for the $CF_3$ resonance (FIG. 6A) and the $CF_2$ resonance (FIG. 6B) of Oxypherol as a function of temperature.
Figure 6B:
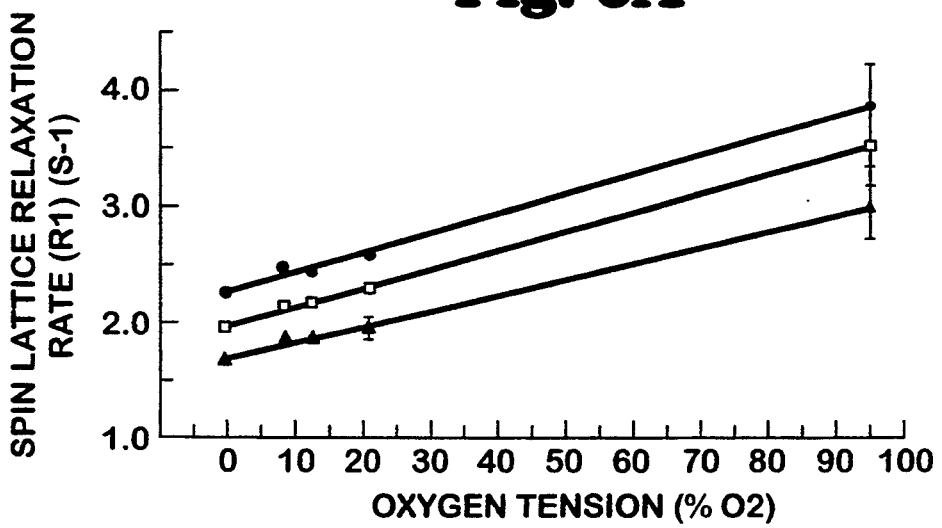

The results again showed that Oxypherol-ET (perfluorotributylamine) has four $^{19}F$ resonances, which are well resolved at 282.3 MHz. Individual $R_1$ measurements were obtained for each resonance. FIG. 6 shows the variation of $R_1$ with oxygen tension, and demonstrates that at any specific temperature there is a linear relationship between $R_1$ and $pO_2$ for each of the resonances. FIG. 6A shows curves for the $CF_3$ resonance and FIG. 6B for the downfield $CF_2$. Separate curves are shown for the temperatures: 27.2° C. ●, 34.2° C. (□), and 40.6° C. (▲). Data at 0, 21, and 95% $pO_2$ represent the mean $\pm$ standard, while 8 and 12% are single determinations.

The equations defining the relationship between $R_1$ and $pO_2$ at each temperature for each of the two downfield resonances are shown in Table 3.

TABLE 3

Dependence of Spin-Lattice Relaxation Rate ($R_1$ ($s^{-1}$)) on Oxygen Tension

| | | | |
|---|---|---|---|
| $CF_3$ | 27.2° C. | $R_1 = 1.99 \times 10^{-2}$ (% $pO_2$) + 1.093 | $r^2 = 0.999$ |
| | 34.2° C. | $R_1 = 1.94 \times 10^{-2}$ (% $pO_2$) + 0.948 | $r^2 = 0.998$ |
| | 40.6° C. | $R_1 = 1.61 \times 10^{-2}$ (% $pO_2$) + 0.815 | $r^2 = 0.997$ |
| $CF_2$ | 27.2° C. | $R_1 = 1.75 \times 10^{-2}$ (% $pO_2$) + 2.244 | $r^2 = 0.996$ |
| | 34.2° C. | $R_1 = 1.69 \times 10^{-2}$ (% $pO_2$) + 1.940 | $r^2 = 0.999$ |
| | 40.6° C. | $R_1 = 1.41 \times 10^{-2}$ (% $pO_2$) + 1.709 | $r^2 = 0.996$ |

Figure 7:
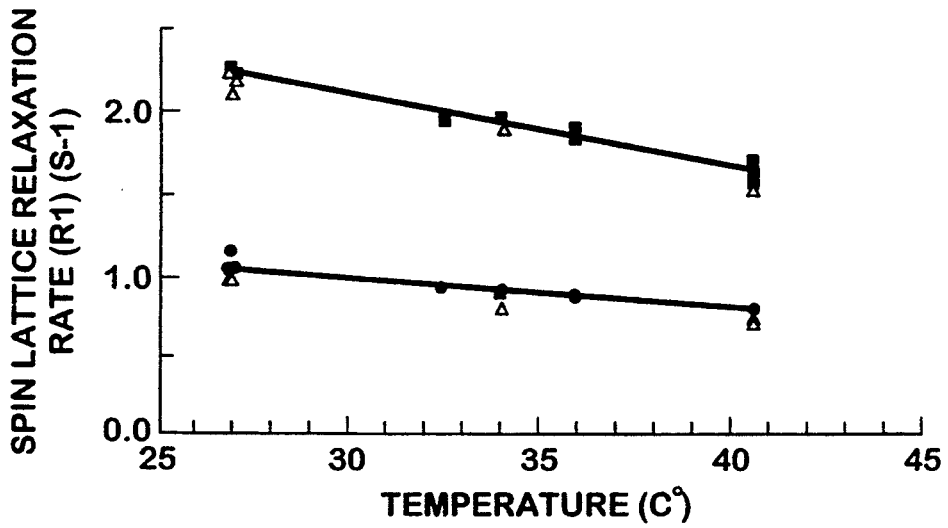
FIG. 7 shows the temperature dependence of the spin-lattice relaxation rate of Oxypherol in the absence of oxygen.

FIG. 7 shows the dependence of the spin-lattice relaxation rate ($R_1$) with respect to temperature, in the absence of oxygen ($pO_2 = 0\%$). Separate curves are shown for each resonance, $CF_3$ ● and $CF_2$ ■. Data from the excised mouse tissues are also shown (△). Similar curves apply in the presence of oxygen. This figure shows that there is a linear relationship between $R_1$ and temperature in the range 27°–40° C. for each resonance. The equations for the two lines are shown in Table 4.

TABLE 4

Dependence of Spin-Lattice Relaxation Rate ($R_1$ ($s^{-1}$)) on Temperature ($pO_2 = 0\%$)

| | | |
|---|---|---|
| $CF_3$ | $R_1 = 1.662 - 2.15 \times 10^{-2}$ (T (°C.)) | $r_2 = 0.934$ |
| $CF_2$ | $R_1 = 3.353 - 4.15 \times 10^{-2}$ (T (°C.)) | $r_2 = 0.960$ |

Data were acquired both during heating and cooling. Significantly, they lie on the same line. The data for excised hypoxic liver and tumor tissue in FIG. 7 also showed a substantial degree of agreement with the calibration curves.

EXAMPLE 3

The relationship between $T_1$ and $pO_2$, temperature, and magnetic field strength was determined for Oxypherol-ET at 37° C. and 7 T, using techniques as described above. Three types of experiments were performed on myocardial tissue: accurate $pO_2$ measurements, ultrafast $pO_2$ determinations, and MRI to assess the distribution of PFC in the heart.

Oxypherol-ET was administered to four Sprague-Dawley rats (1 ml per 100 g daily iv in the tail for 8 days). One week after the final infusion of Oxypherol-ET, the PFC-loaded heart was excised and perfused with Krebs-Henseleit buffer at 37° C. using Langendorff retrograde perfusion. The perfusate was equilibrated with carbogen (95% $O_2$, 5% $CO_2$). To remove blood and any residual blood-borne PFC, the initial 10 min. of perfusion was performed with nonrecycling medium.

The temperature was monitored using a microthermocouple (Sensortek, Clifton, N.J.) in the perfusion medium close to the heart. Fluorine spectra were acquired at 282 MHz using a 20 mm NMR probe (VSP, Bruker, Billerica, Miss.) is a Nicolet NT 300 (7 T) NMR spectrometer. This gave a pulse width $^{19}F$ $(\pi/2) \approx 120$ $\mu s$. Shimming was accomplished on the sodium signal to a typical linewidth of $\approx 13$ Hz ($^{23}Na$).

For the accurate $pO_2$ determination, the spectrometer frequency was placed midway between the downfield $CF_3$ and $CF_2$ resonances. The spin-lattice relaxation times of the two resonances were determined using a pulse-burst saturation recovery pulse sequence. Following a 100 $\mu s$ (90°) pulse 1K data points were acquired across a spectral width of $\pm 1.4$ KHz. A 40 Hz exponential line broadening was applied prior to Fourier transformation. Spectra were acquired with 14 delay times in the range of 25 ms to 12 s and four acquisitions per delay requiring a total of 2.5 min.

For the ultrafast $pO_2$ determination, $T_1$ was estimated using a two-point determination which provided a time resolution of 1.2 s. Under conditions of rapid pulsing ($T_R < 5T_1$, where $T_R$ is the repetition time), the signal was subject to partial saturation and the observed intensity (I) was related to the fully relaxed intensity ($I_0$) by the expression $$I = I_0[1 - exp(-T_R/T_1)]$$

With $T_R$ held constant, changes in $T_1$ produced changes in I, allowing the monitoring of dynamic changes in $pO_2$ during the onset of global ischemia.

For the MRI experiments, the heart was examined by proton ($^1H$) and $^{19}F$ NMR imaging. A balloon filled with $D_2O$ was inserted into the left ventricle and the heart was also suspended in $D_2O$. Imaging was performed using an Omega 9.4 T NMR spectrometer (GE, Fremont, Calif.) with self-shielded Acustar gradient coils and a home-built 25 mm i.d. Helmholtz coil tunable to both $^1H$ and $^{19}F$. The probe was tuned to 400 MHz for proton MRI. Images were acquired as a three dimensional spin-echo data set (256*256*8) with $T_R = 500$ ms, $T_E = 20$ ms, and the 230 $\mu m$ in-plane resolution with 2.5 mm slice thickness. The pulse width was 200 $\mu s$ (90°) and four acquisitions were acquired for each increment. The corresponding $^{19}F$ images were also acquired as a three-dimensional spin-echo data set with additional driven-equilibrium pulses to enhance acquisition efficiency and produce a PFC density map. The $^{19}F$ imaging parameters were $T_R = 75$ ms, $T_E = 5$ ms, and a 460 $\mu m$ in-plane resolution with 2.5 mm slice thickness. With the probe tuned to 376.47 MHz a 170 $\mu s$ (90°) pulse was used with 900 acquisitions per increment requiring a total of 19 hours for the three-dimensional acquisition.

Figure 8:
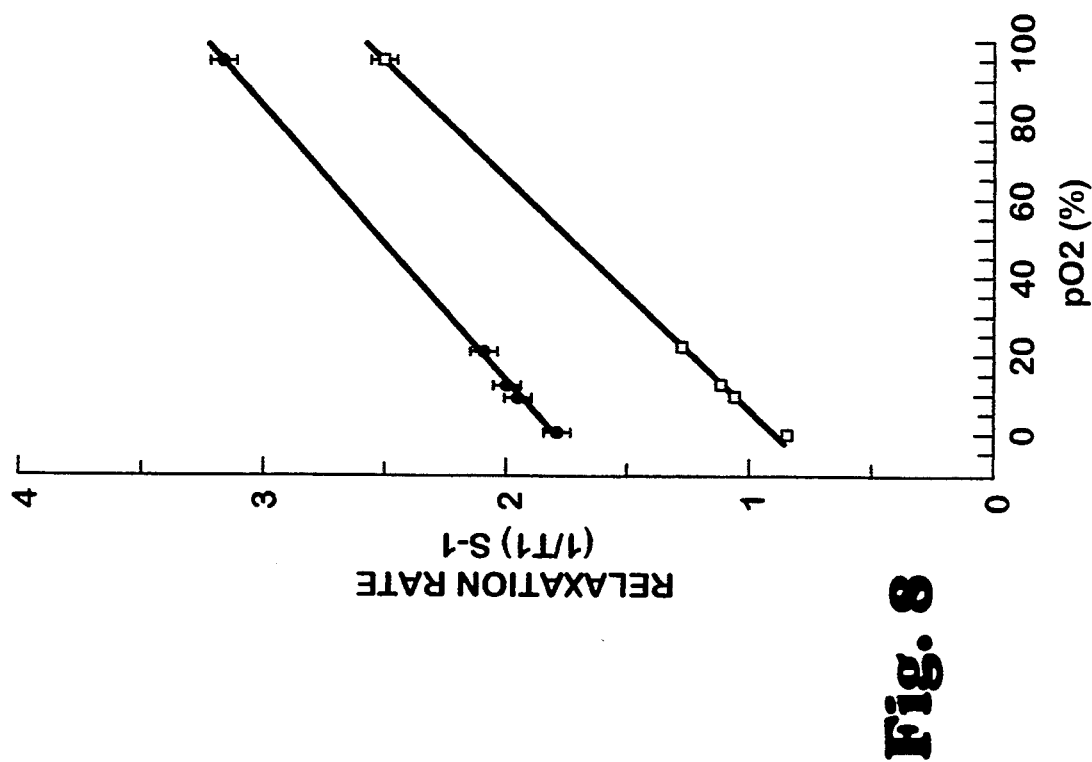
FIG. 8 shows the variation of spin-lattice relaxation rate with $pO_2$ for Oxypherol at 37° C. and 7 Tesla.

The results showed a linear relationship between $R_1$ and $pO_2$ for each resonance as shown in FIG. 8 ($CF_3$ □ and $CF_2$ ●; values represent means of three individual determinations; error bars indicate standard errors of the mean), and in Table 5 below.

TABLE 5

| | Dependence of Spin-Lattice Relaxation Rate ($R_1$) on Oxygen Tension at 37° C.* | | | |
|---|---|---|---|---|
| | a b | r | α | β |
| $CF_3$ | $R_1 = 0.88 + 0.0172$ (% $pO_2$) | > 0.999 | ± 0.012 | ± 0.0003 |
| $CF_2$ | $R_1 = 1.80 + 0.0145$ (% $pO_2$) | > 0.997 | ± 0.021 | ± 0.0005 |

*a = intercept ($s^{-1}$), b = slope ($s^{-1}$/% $pO_2$), r = correlation coefficient, α = standard error of the intercept ($s^{-1}$), β = standard error of the slope ($s^{-1}$/% $pO_2$), $R_1$ = spin-lattice relaxation rate ($s^{-1}$), $pO_2$ = oxygen tension (% atmosphere)

Figure 9:
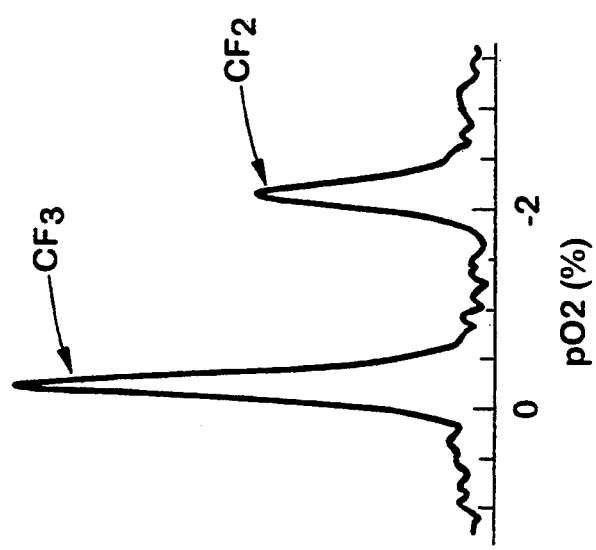
FIG. 9 shows the $^{19}F$ spectrum of the downfield $CF_3$ and $CF_2$ resonances of the $CF_3$ and $CF_2$ (2 ppm) resonances of Oxypherol sequestered in a perfused rat heart.

Heart functions (rate, developed pressure, coronary flow) and $^{31}P$ NMR spectra appeared normal. An intense $^{19}F$ signal was obtained in one acquisition and the resonances of perfluorotributylamine were clearly resolved in the perfused heart, as shown in FIG. 9. For the $CF_3$ resonance, $T_1 = 549$ ±15 ms (n=4) (mean ±SD, n=number of hearts), and for $CF_2$, $T_1 = 387$ ±30 ms, which corresponds to $pO_2 = 54.8$ ±3.1 and 54.7 ±14.1%, respectively, giving a mean value of 54.8 ±9.4% ($\approx 416$ Torr). The signal/noise ratio was greater than 20 and the resonances were well resolved. A second measurement 10 min. later gave essentially identical values.

Figure 10A:
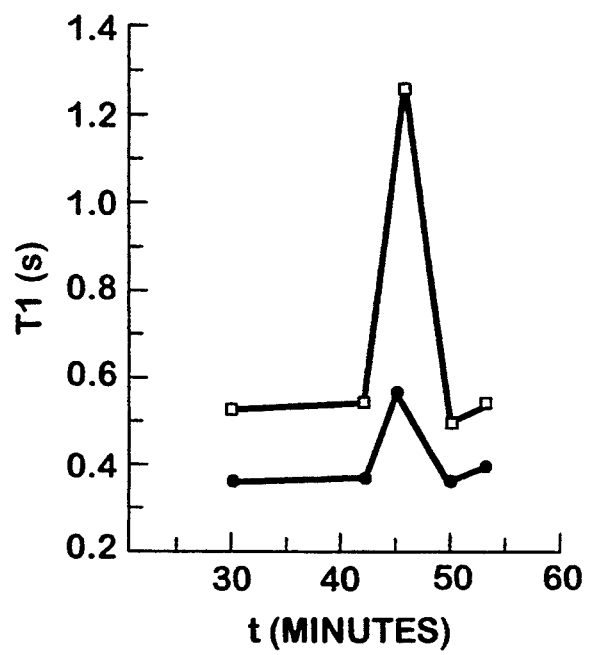
FIG. 10 shows the variation of spin-lattice relaxation time (FIG. 10A) and calculated myocardial oxygen tension (FIG. 10B) with global ischemia and reperfusion for a rat heart.
Figure 10B:
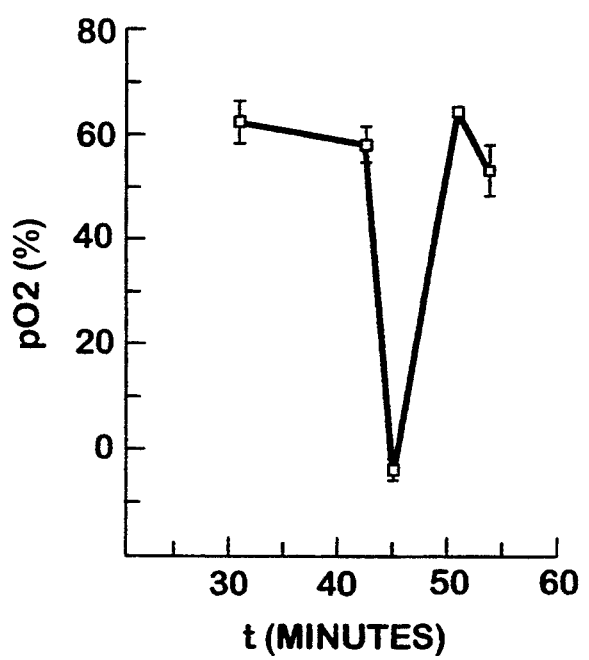

Perfusion was stopped, inducing total global ischemia, and 2 min. later $T_1$'s were again determined. The $T_1$ of each of the resonances increased; for $CF_3$, 1221 ±61 ms, and for $CF_2$, 569 ±58 ms, corresponding to $pO_2 = -3.6$ ±2.3 and $-2.3$ ±12.2%, respectively, giving a mean value of $-3.0$ ±8.2%. After 8 min. of global ischemia, the heart was reperfused and the new $T_1$ values indicated substantial reoxygenation. FIG. 10 shows the variation in the $T_1$'s and calculated $pO_2$'s for a typical heart. FIG. 10A shows the variation in $T_1$ for each resonance $CF_3$ (□) and $CF_2$ ●. FIG. 10B shows the mean $pO_2$ derived from the $T_1$'s of the $CF_3$ and $CF_2$ resonances. The normoxic heart showed a high stable $pO_2$ ($\approx 60\%$, $\approx 450$ Torr). During ischemia $pO_2$ fell to 0%, i.e. hypoxia. Upon reperfusion there was substantial reoxygenation and $pO_2$ returned to its initial value.

Complete loss of oxygen occurred within the time required to make these measurement (2.5 min.), indicating the need for enhanced time resolution to determine the dynamics of oxygen loss.

Figure 11A:
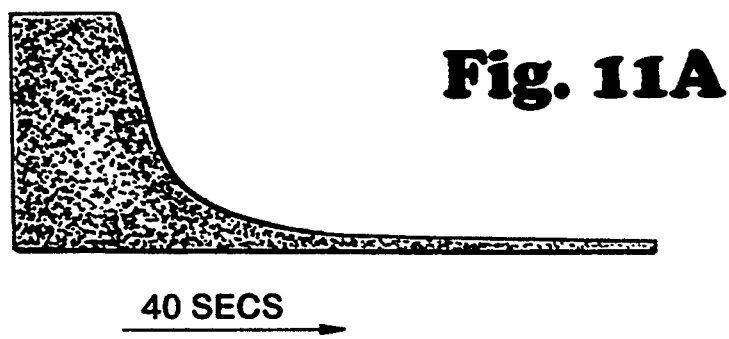
FIG. 11 shows in the lower trace the variation of $pO_2$ during the onset of global ischemia in a rat heart. The upper trace shows the corresponding ventricular pressure.
Figure 11B:
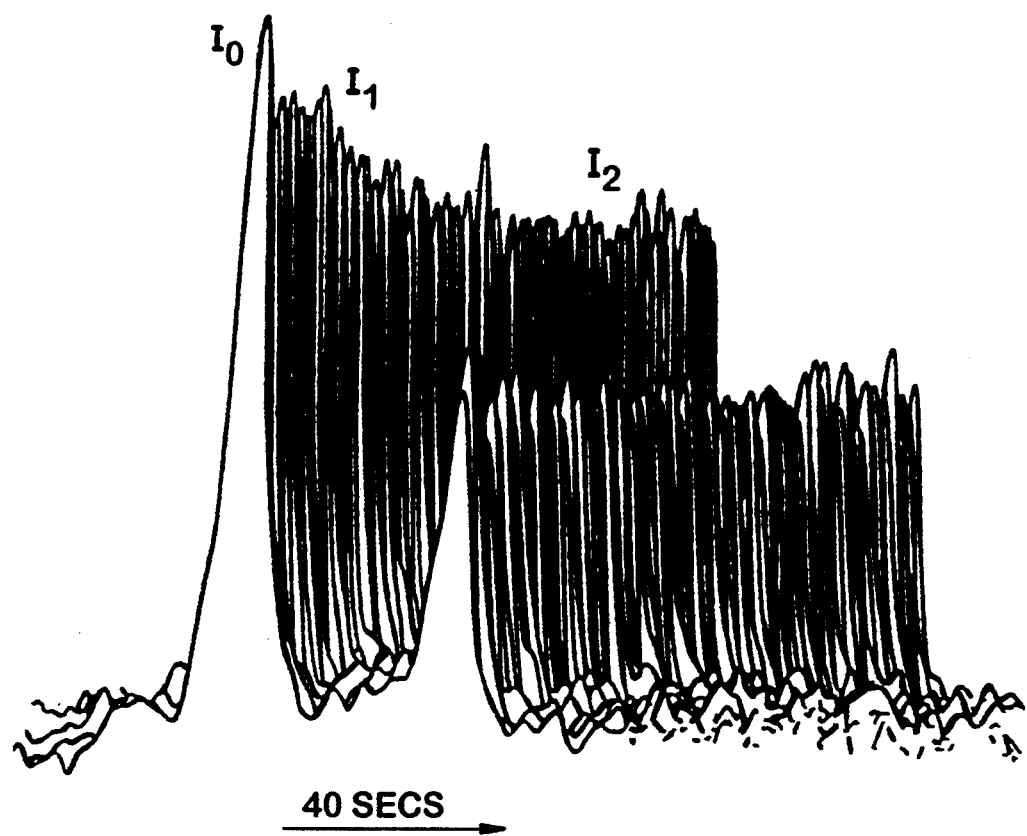

Rapid dynamic changes in $pO_2$ were observed using a series of partial-saturation spectra. FIG. 11 shows the dynamic changes in signal intensity with the onset of global ischemia; loss of oxygen from a perfused rat heart was complete within 40 s. The initial peak shows the fully relaxed signal intensity ($I_0$). The initial plateau ($I_1$) results from spectra acquired during normal perfusion ($I_1/I_0=0.86 \pm 0.06$, $T_1=610 \pm 100$ ms, $pO_2=44 \pm 14\%$). The onset of ischemia caused rapid loss of signal intensity and hypoxia was evident within 40 s, giving a new steady state ($I_2/I_0=0.68 \pm 0.06$, $T_1=1050 \pm 200$ ms, $pO_2=4.2 \pm 8\%$). This rapid change indicates the importance of high temporal resolution in monitoring dynamic changes in cardiac $pO_2$. The upper trace shows the corresponding ventricular pressure, indicating close correlation between pressure and $pO_2$.

These values were in substantial agreement with $T_1$ determinations made in the same heart using PBSR immediately before and after the partial saturation experiment; i.e. $T_1$ (perfused)=540 ms and $T_1$ (ischemic)=1240 ms. There was minimal change in the partial saturation intensity of the $CF_2$ resonance with the onset of ischemia due to the shorter $T_1$'s. There was close correlation between oxygen tension and observed ventricular pressure. Following 8 min. of global ischemia, reperfusion provided extensive reoxygenation and $pO_2$ returned to its initial value within 1 min. Extended ischemia (1 hour) led to contracture and minimal reoxygenation upon reflow.

Proton and $^{19}F$ NMR images of the heart indicated that PFC was distributed throughout the heart.

EXAMPLE 4

The relationship ($R_1 \propto pO_2$) was determined experimentally for Oxygent (90% w/v emulsion perflubron) using techniques similar to those described above. Standard gases (0–100% $O_2$, where $100\% \approx 760$ Torr) were bubbled through aliquots of Oxygent in order to obtain specific oxygen concentrations and the samples were placed in gas-tight NMR tubes. NMR experiments were conducted in a 4.7 T CSI spectrometer with $^{19}F$ at 188.3 MHz. $R_1$ was determined using pulse-burst saturation recovery experiments on the downfield resonances (18 and 0 ppm) and on the upfield resonances separately. The variation of $R_1$ with temperature was examined in the range 27°–37° C.

Additionally, a Dunning prostate adenocarcinoma R3327-AT1 was implanted in a pedicle on the fore-back of a Copenhagen rat. When the tumor reached about 1.5 cm diameter a total of 20 ml Oxygent was infused IV into the tail of the rat over a period of one week. Four days after the final dose, following complete vascular clearance of Oxygent the rat was anesthetized (2:1::$N_2O$:$O_2$+0.5% methoxyflurane) and the tumor observed by $^{19}F$ NMR spectroscopy with a coil around the tumor. The rectal temperature was measured using an optical fiber probe. In addition the tumor was imaged by $^1H$ and $^{19}F$ MRI to determine the distribution of PFC in the tumor.

Figure 12:
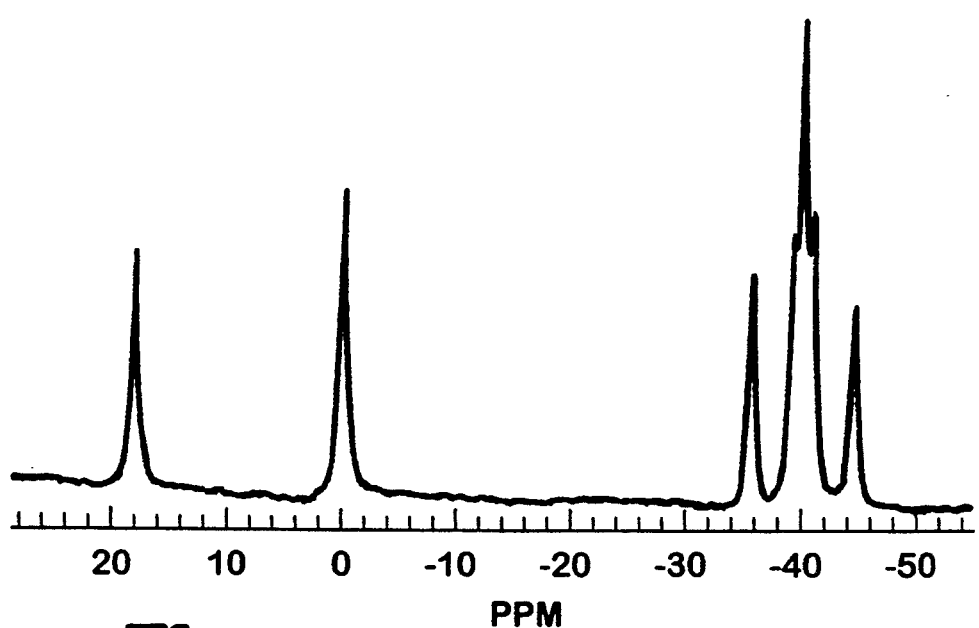
FIG. 12 shows the $^{19}F$ NMR spectrum of Oxygent (an emulsion of perflubron [perfluorooctylbromide]) in a tumor.
Figure 13:
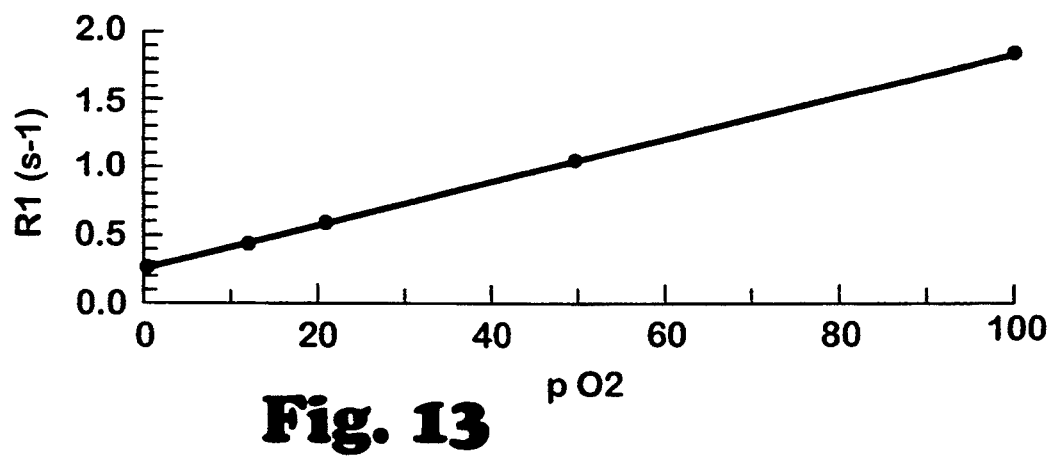
FIG. 13 shows the variation of $^{19}F$ NMR spin-lattice relaxation rate with $pO_2$ for the $CF_3$ resonance of Oxygent.

The $^{19}F$ NMR spectrum of Oxygent showed five well resolved signals in the tumor in vivo at 4.7 T, as shown in FIG. 12. A linear relationship between spin-lattice relaxation rate and oxygen tension ($R_1$ ($s^{-1}$)=m%$pO_2$+c) was determined for each signal at 37° C., as shown in Table 6 and FIG. 13. The data points in FIG. 13 ● represent the $CF_3$ resonance (0 ppm).

TABLE 6

| | | Relationship $R_1 = f(pO_2)$ at 37° C. | | | |
|---|---|---|---|---|---|
| Emulsion | Resonance | Chem. Shift ppm | Intercept (c) $s^{-1}$ | Slope (m) $s^{-1}/\%$ | Sensitivity $\eta = m/c$ |
| Oxygen 4.7 T | $CF_2Br$ | 18 | $R_1 = 0.2893 + 1.52 \times 10^{-2}$ (% $pO_2$) | | 5.3 |
| | $CF_3$ | 0 | $R_1 = 0.2677 + 1.61 \times 10^{-2}$ (% $pO_2$) | | 6.0 |
| | | −36 | $R_1 = 0.2762 + 1.50 \times 10^{-2}$ (% $pO_2$) | | 5.4 |
| | | −40 | $R_1 = 0.3840 + 1.48 \times 10^{-2}$ (% $pO_2$) | | 3.9 |
| | | −45 | $R_1 = 0.2890 + 1.54 \times 10^{-2}$ (% $pO_2$) | | 5.3 |
| Oxygent 7 T | $CF_3$ | 0 | $R_1 = 0.290 + 1.73 \times 10^{-2}$ (% $pO_2$) | | 6.0 |
| Oxypherol 4.7 T | $CF_3$ | 0 | $R_1 = 0.779 + 1.75 \times 10^{-2}$ (% $pO_2$) | | 2.2 |

Figure 14:
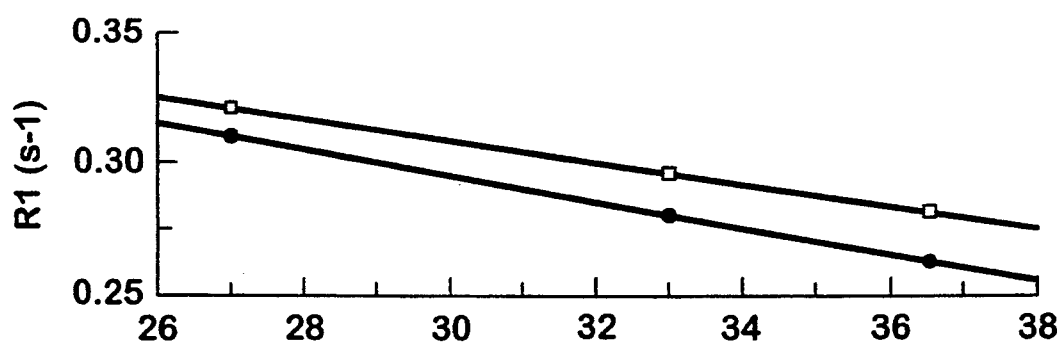
FIG. 14 shows the variation of spin-lattice relaxation rate with temperature in the absence of oxygen for the $CF_3$ and $CF_2$ resonances of Oxygent.

$R_1$ is not only dependent on $pO_2$ but also has a linear relationship with temperature, as shown in Table 7 and FIG. 14. The data points in FIG. 6 represent the $CF_3$ resonance ● $R_1=0.444-4.97\times10^{-3}$ (T(°C.))) and the $CF_2Br$ resonance (□, $R_1=0.432-4.10\times10^{-3}$ (T(°C.))), both in the absence of oxygen ($pO_2=0\%$).

TABLE 7

| Influence of Temperature on Relationship $R_1 = f(pO_2)$ for Oxygent at 4.7 T | | | |
|---|---|---|---|
| Resonance | Intercept (c) $s^{-1}$ | Slope (m) $s^{-1}/\%$ | Temperature °C. |
| $CF_2Br$ | $R_1 = 0.3374 + 1.71 \times 10^{-2}$ (% $pO_2$) | | 27 |
| $CF_2Br$ | $R_1 = 0.3152 + 1.54 \times 10^{-2}$ (% $pO_2$) | | 33 |
| $CF_2Br$ | $R_1 = 0.2893 + 1.52 \times 10^{-2}$ (% $pO_2$) | | 36.6 |
| $CF_3$ | $R_1 = 0.3018 + 1.836 \times 10^{-2}$ (% $pO_2$) | | 27 |
| $CF_3$ | $R_1 = 0.2772 + 1.797 \times 10^{-2}$ (% $pO_2$) | | 33 |
| $CF_3$ | $R_1 = 0.2677 + 1.613 \times 10^{-2}$ (% $pO_2$) | | 36.6 |

In the AT1 tumor, $R_1$ ($CF_3$)=0.40 $s^{-1}$ and $R_1$ ($CF_2Br$)=0.40 $s^{-1}$ were measured. The rectal temperature was 33° C. and thus, using the calibration curves from Table 7, $pO_2$ was estimated as 6.9% and 5.5% respectively or $\approx 45$ Torr. $^{19}F$ MRI indicated that Oxygent was distributed throughout the tumor, with highest density close to the periphery.

Using a sensitivity index ($\eta$=slope/intercept) it appears that the resonances at 18 ppm ($CF_2Br$) and 0 ppm ($CF_3$) are the most sensitive to changes in $pO_2$. There is very little difference between the calibration curves at 4.7 T and those previously determined at 7 T. However, note that application of the 7 T curves to the current data would produce an error $\approx 15$ Torr, which is radiobiologically significant.

The sensitivity to $pO_2$ of each of the Oxygent signals is considerably greater than that of the most sensitive signal of Oxypherol, as shown in Table 6. At the same time Oxygent is far less sensitive to changes in temperature, so that small errors in temperature measurement produce less error in $pO_2$ estimation. For example, a 2° C. error in temperature estimation gives an error of 0.6% (5 Torr) for Oxygent, whereas an error of $\approx 15$ Torr is typical for Oxypherol. The large separation of the $CF_3$ and $CF_2Br$ resonances ensures the signals are resolved even at lower magnetic field and permits individual $R_1$ estimates to be obtained. This provides independent estimates of $pO_2$, enhancing the confidence in the result. The wide separation of the resonances also facilitates chemical shift selective imaging, avoiding chemical shift artifacts.

EXAMPLE 5

The relationship $R_1 \propto pO_2$ was determined for Oxygent at 37° C. and 7 Tesla using techniques generally like those described above. Standard gases were bubbled through aliquots of Oxygent in order to obtain specific oxygen concentration and the samples were placed in gas-tight NMR tubes. Pulse-burst saturation recovery experiments were performed on the downfield resonances (18 and 0 ppm) and on the upfield resonances separately. $R_1$ was estimated using a three parameter fit. The variation of $R_1$ with temperature was examined in the range 4°–50° C.

Also, Oxygent was administered to a mouse (3×500 μl over 5 days). Four days later the mouse was anesthetized and placed with a surface coil against the chest to observe the liver and spleen. $R_1$ was determined using techniques as described above and the rectal temperature was monitored using a Luxtron fiber optic probe.

Figure 15:
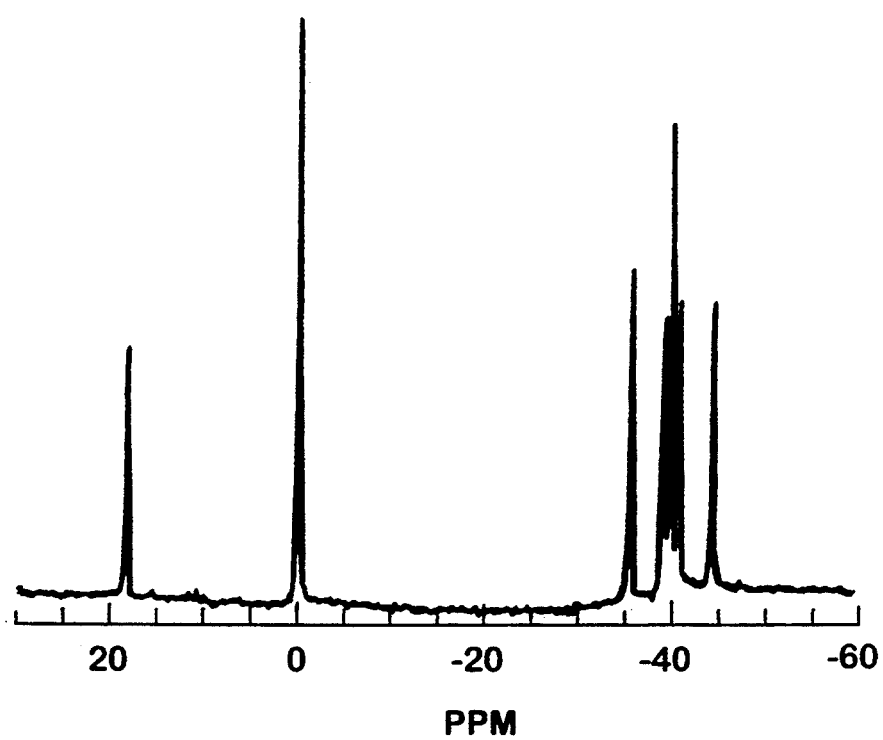
FIG. 15 shows a $^{19}F$ spectrum of Oxygent.

The $^{19}$F NMR spectrum of Oxygent (PFOB) had seven well-resolved signals as shown in FIG. 15. Each resonance showed a linear relationship between spin-lattice relaxation rate and oxygen tension at 37° C. as shown in Table 8.

TABLE 8

| Emulsion | Resonance Chem. shift ppm | Intercept (c) $s^{-1}$ | Slope (m) $s^{-1}/\%$ | Sensitivity $\eta$ (m/c) |
| --- | --- | --- | --- | --- |
| Oxygent | 18 | $R_1 = 0.354 + 1.72 \times 10^{-2} (\% pO_2)$ | | 4.7 |
| | 0 | $R_1 = 0.290 + 1.73 \times 10^{-2} (\% pO_2)$ | | 6.0 |
| | −36 | $R_1 = 0.415 + 1.54 \times 10^{-2} (\% pO_2)$ | | 3.7 |
| | −39 | $R_1 = 0.613 + 1.58 \times 10^{-2} (\% pO_2)$ | | 2.6 |
| | −40 | $R_1 = 0.614 + 1.51 \times 10^{-2} (\% pO_2)$ | | 2.5 |
| | −41 | $R_1 = 0.586 + 1.47 \times 10^{-2} (\% pO_2)$ | | 2.5 |
| | −45 | $R_1 = 0.455 + 1.56 \times 10^{-2} (\% pO_2)$ | | 3.4 |
| Oxypherol | 0 | $R_1 = 0.886 + 1.72 \times 10^{-2} (\% pO_2)$ | | 1.9 |

Figure 16:
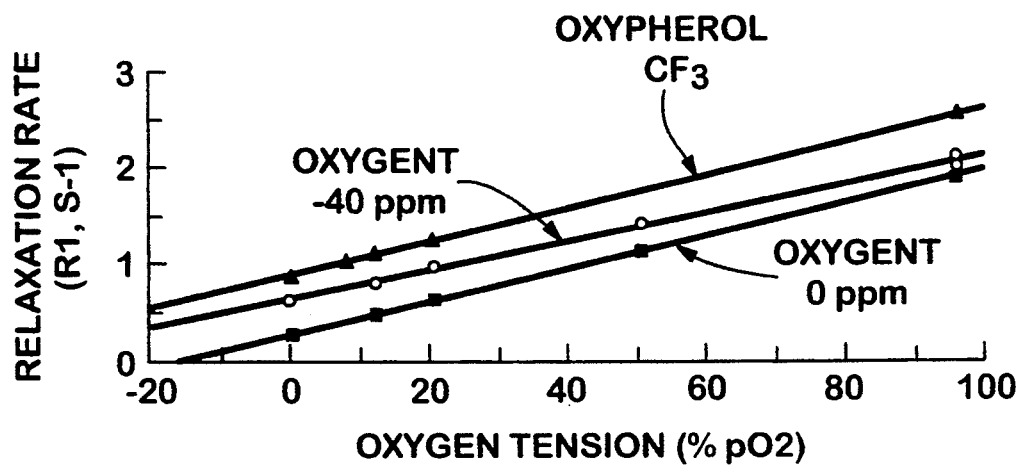
FIG. 16 shows the variation of relaxation rate with $pO_2$ for certain resonances of Oxygent and Oxypherol.
Figure 17:
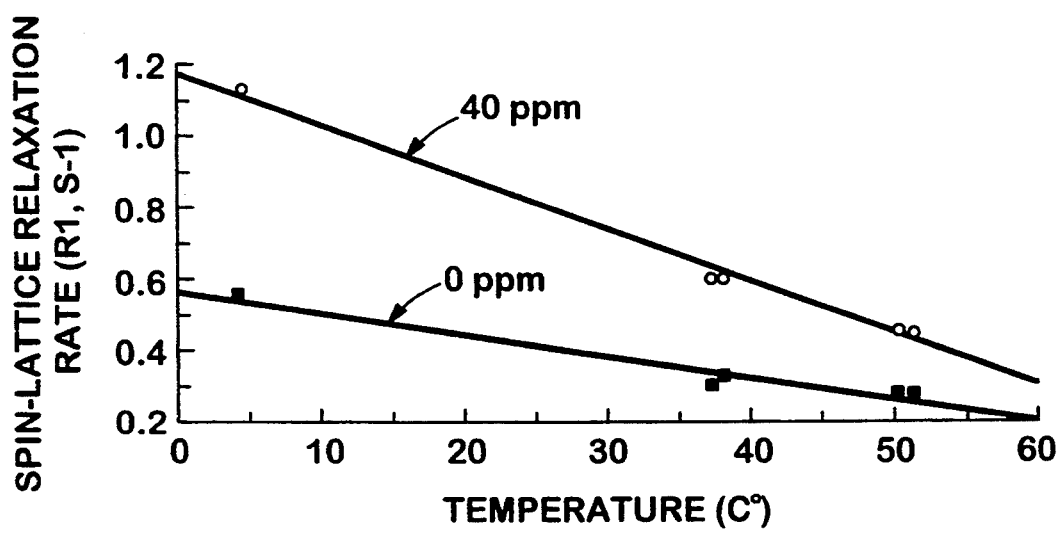
FIG. 17 shows the variation of spin-lattice relaxation rate with temperature in the absence of oxygen for two resonances of Oxygent.
Figure 18A:
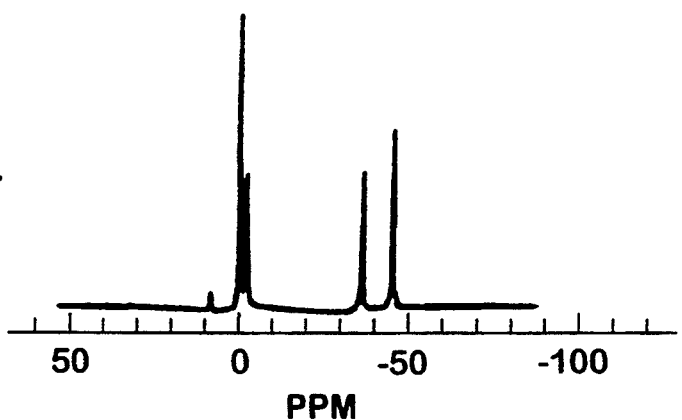
FIGS. 18A through 18D show $^{19}F$ NMR spectra for the commercial PFC emulsions Oxypherol (emulsion of perfluorotributylamine) (18A), Oxygent (emulsion of perflubron) (18B), Therox (emulsion of bis-perfluorotripropylamine) (18C), and Fluosol (mixed emulsion of perfluorotripropylamine and perfluorodecalin) (18D).
Figure 18B:
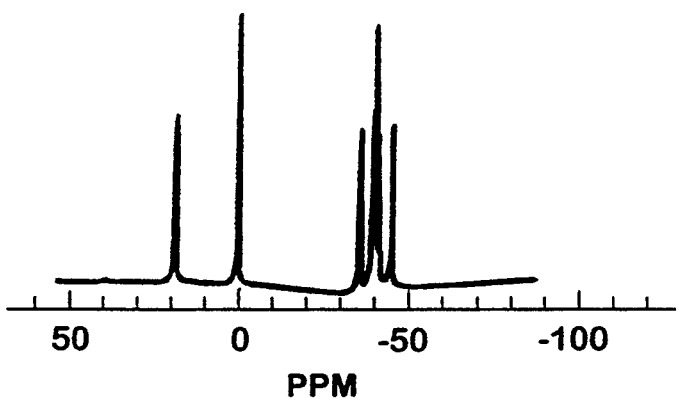
Figure 18C:
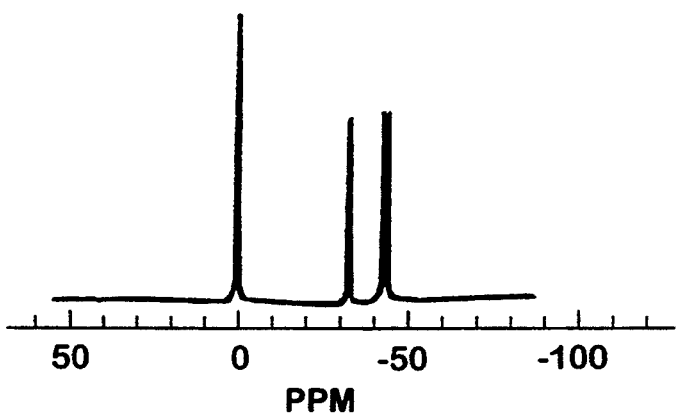
Figure 18D:
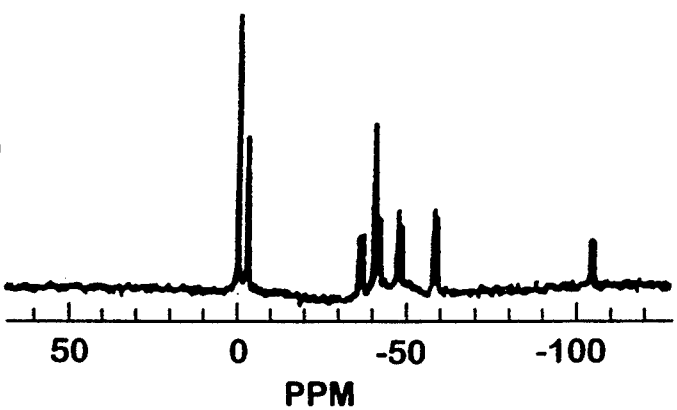

FIG. 16 graphically compares the linear relationship for the most and least sensitive resonances of Oxygent with Oxypherol. (Oxygent 0 ppm ■, Oxygent −40 ppm (○), and Oxypherol CF$_3$ ▲.) FIG. 17 shows the variation of spin-lattice relaxation rate with temperature in the absence of oxygen, for Oxygent resonances at 0 ■ and 40 ppm (○).

When the mouse had a core temperature of 28.2° C., $R_1$ values of 0.69 s$^{-1}$ and 0.65 s$^{-1}$ were found for the resonances at 18 and 0 ppm, respectively. These values indicated $pO_2 = 14\%$ and 14.5% respectively, or about 100 Torr.

EXAMPLE 6

$^{19}$F relaxometry of an Oxygent PFC emulsion sequestered in rat tumor tissue at 4.7 T and 33° C. showed that the most sensitive resonance of Oxygent (perflubron) (CF$_3$) showed a relationship $R_1 = 0.277 + 0.018 (\%pO_2)$, which is considerably more sensitive than $R_1 = 0.868 + 0.018(\%pO_2)$ for Oxypherol (CF$_3$). Moreover, perflubron was relatively insensitive to interference from tissue temperature ($R_1 = 0.44 - 0.005$(°C.)) vs. $R_1 = 1.38 - 0.0169$(°C.) for Oxypherol at 0% $pO_2$). In addition, the most sensitive resonances in perflubron (CF$_3$ and CF$_2$Br) remain well resolved at 4.7 T ($\Delta\delta \approx 18$ ppm), whereas CF$_3$ may overlap the downfield-CF$_2$ (the least sensitive resonance in Oxypherol) particularly in heterogenous tissue such as tumor.

EXAMPLE 7

Representative 282 MHz $^{19}$F NMR spectra of four commercial PFC emulsions are compared in FIG. 18A–18D. The emulsions are: (a) Oxypherol (20% w/v emulsion of perfluorotributylamine), (b) Oxygent (90% w/v emulsion perflubron), (c) Therox (40% w/v emulsion of trans-1,2 bis-(perfluorobutyl)-ethylene), and (d) Fluosol (emulsion of 14% w/v perfluorodecalin and 6% w/v perfluorotripropylamine (PFTP)). The CF$_3$ resonance of each emulsion is essentially coincident and is set to 0 ppm. There is some confusion in the literature regarding spectral assignments, and it may be preferable to refer to resonances by the chemical shift. CF$_2$'s occur ≈40 ppm upfield, while CF$_2$X (hetero-nucleus) are shifted downfield.

EXAMPLE 8

Oxypherol was administered (4×4 ml over 2 days) to a Copenhagen rat which had a Dunning prostatic adenocarcinoma AT1 grown in a skin pedicle on its foreback. $^{19}$F MRI showed that the PFC was extensively distributed throughout the tumor immediately after administration. Two days later the clearance of the PFC from the vasculature was complete. Over the next 16 days, the tumor doubled in diameter. However, comparison of sequential $^{19}$F MRI images showed that the PFC remained in the central tumor tissue and did not redistribute.

Using a volume coil around the tumor, $^{19}$F spectroscopy determined $R_1 = 1.013$ s$^{-1}$ (32° C.), indicating $pO_2 \approx 90$ Torr. As the tumor grew, $pO_2$ declined to 30 Torr 12 days after administration and to 0 Torr by day 16. This corresponded with the predicted onset of central tumor hypoxia.

EXAMPLE 9

The following NMR experiments were performed using a Nicolet NT300 (7 T) spectrometer, and using the perfluorocarbon emulsion Oxypherol-ET (prepared according to the manufacturer's instructions). For calibration experiments, standard gases having specific oxygen tensions (0%, 8%, 12.2% 21% and 95% O$_2$, with 100% = 760 Torr) were prepared as described above. The samples were placed in gas tight 5 mm NMR tubes and $^{19}$F NMR spectra were obtained at 282 MHz. Temperature was carefully regulated using an FTS TC 44 variable temperature unit (Stone Ridge, N.Y.), together with the Nicolet variable temperature unit incorporated in the NMR system. The 5 mm probe was allowed to equilibrate until a stable temperature was observed ($\geq \frac{1}{2}$ hour) using a thermocouple (Sensortek Corp., Clifton, N.J.) inserted in the probe. Once equilibrium was achieved, the temperature was found to be stable within ±0.1° C. over ½ h. Each sample of Oxypherol-ET was allowed to equilibrate for more than 10 min. in the probe, this being adequate to achieve the stable desired temperature prior to NMR observation.

$R_1$ was determined in 81 samples at 14 different temperatures in the range 27°–50° C. An additional data set was acquired at 5° C. Spin-lattice relaxation rates were determined generally as described above. Separate pulse-burst saturation recovery (PBSR) experiments were performed on the downfield $CF_3 + \beta\text{-}CF_2$ resonances and the two upfield $CF_2$s with the spectrometer frequency placed midway between the pair of resonances. $R_1$ was estimated using a three-parameter fit. Linear regression analysis was performed to determine the relationships between $R_1$, $pO_2$, and temperature, and standard errors of slopes and intercepts were assessed.

In addition, the following in vivo experiments were performed. A Meth-A tumor-bearing BALB/C mouse was injected with Oxypherol-ET (3×1 ml, IV) over three days. Following complete vascular clearance of the PFC (six days), the mouse was anesthetized and the tumor placed against a 1.8 cm surface coil. $R_1$ values were determined for the sequestered PFC using PBSR, generally as described above.

Oxypherol-ET was also administered to a rat (1 ml/100 g daily IV in the tail for eight days). The PFC-loaded heart was excised and perfused with Krebs-Henseleit buffer at 37° C. using Langendorff retrograde perfusion. In order to remove blood and any residual blood-borne PFC, the initial 10 min. of perfusion were performed with nonrecycling medium. Fluorine spectra of sequestered PFC were acquired using a 20 mm NMR probe.

Further, in order to verify that calibration curves determined in solution are applicable in tissue, a PFC-loaded liver was excised from a rat which had been dosed with Oxypherol as described for the heart studies above. Slices of hypoxic liver were suspended in water and $^{19}F$ relaxation rate experiments were performed at 31° C., 44° C., and 5° C., as described for the calibration experiments.

In addition, an Oxypherol-loaded heart was perfused as described above. 15 mM KCl was included in the perfusate to arrest the heart. The heart was cooled and maintained at 5° C. using chilled perfusate and the external variable temperature unit. Mini Clark oxygen electrodes (Diamond General, Ann Arbor, Mich.) connected to a Yellow-Springs monitor (Yellow Springs, Ohio) were placed in the perfusate at the point of cannulation (arterial $pO_2$, $AO_2$) and in the right ventricle to detect coronary sinus effluent (venous $pO_2$, $VO_2$). A fiber optic temperature probe (Luxtron, Mountain View, Calif.) was placed in the perfusate close to the heart to independently monitor temperature. The perfusate was saturated with various gases (0%, 12.2%, 50%, and 95% $O_2$), and following a period of equilibration the $^{19}F$ $R_1$s were determined together with $AVO_2$.

As to the results, assessment of the variation in intercept and slope with temperature of the linear oxygen dependence ($R_1 = a + bpO_2$) indicated the three-dimensional relationship $R_1 = f(T, pO_2)$. A relationship assuming linear dependence upon oxygen tension and temperature as well as a mixed term gave an excellent fit to the data, as given for each resonance in Table 9.

TABLE 9

| | Dependence of $R_1$ on $pO_2$ and Temperature for the Form $R_1 = A + BT + CpO_2 + DTpO_2$ | | | |
|---|---|---|---|---|
| | A B C D | $\alpha^a$ $\beta^a$ $\gamma^a$ | | $\delta^a$ |
| $CF_3$ | $R_1 =$ 1.647 − 0.021 T + 0.027 P − 0.000208 PT | 0.011 0.001 0.00077 | | 0.00006 |
| $\beta\text{-}CF_2$ | $R_1 =$ 3.363 − 0.043 T + 0.027 P − 0.000284 PT | 0.024 0.002 0.0012 | | 0.00012 |
| $\gamma\text{-}CF_2$ | $R_1 =$ 2.967 − 0.038 T + 0.021 P − 0.000131 PT | 0.013 0.001 0.00039 | | 0.00004 |
| $\alpha\text{-}CF_2$ | $R_1 =$ 2.432 − 0.030 T + 0.029 P − 0.000290 PT | 0.016 0.002 0.0012 | | 0.000097 |

$^a$Standard error of the respective coefficient

Thus, if temperature or $pO_2$ is known, then the other parameter is readily obtained from the formulae. However, if neither is known then there is a family of solutions represented by an $R_1$ isocontour, e.g., $R_1$ in FIG. 19.

The equations in Table 9 show that each resonance behaves uniquely with respect to oxygen tension and temperature. Thus, it is possible to solve a pair of simultaneous equations for $pO_2$ and temperature from a pair of $R_1$s.

Figure 19:
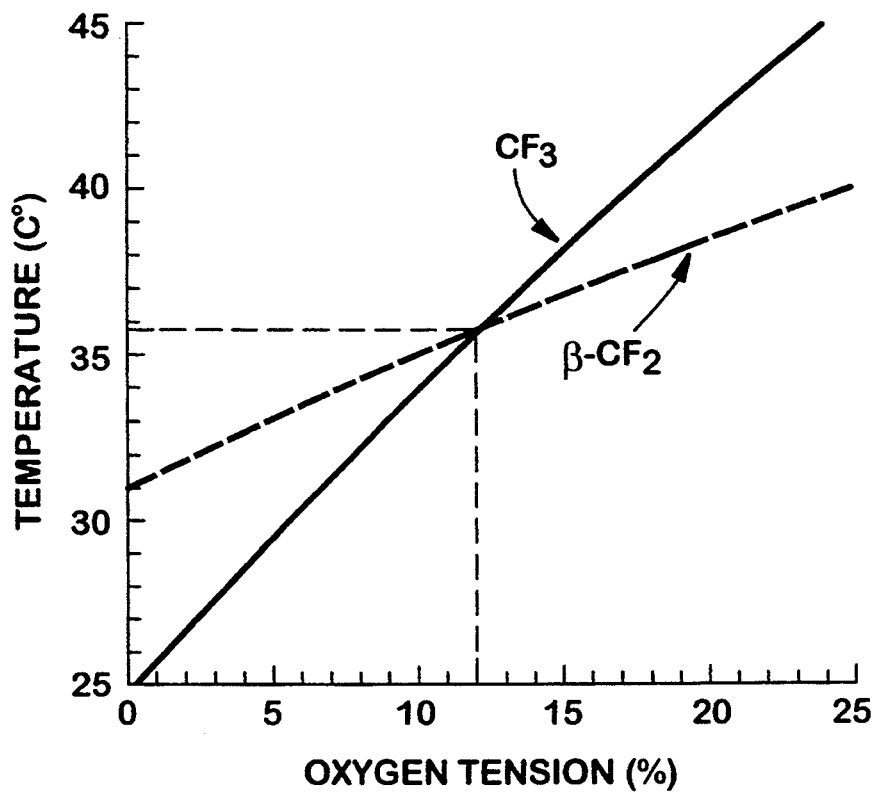
FIG. 19 shows the relationship of oxygen tension and temperature with respect to two different resonances of Oxypherol-ET, and shows how $pO_2$ and temperature may be simultaneously determined.

This is shown graphically in FIG. 19. Isocontours are shown for $CF_3$ (solid) ($R_1 = 1.12 \pm 0.08$ s$^{-1}$) and $\beta\text{-}CF_2$ (dotted) ($R_1 = 2.028 \pm 0.01$ s$^{-1}$) resonances. The intersection of the $CF_3$ and $\beta\text{-}CF_2$ isocontours defines $pO_2$ and temperature. In this case the standard emulsion has $pO_2 = 12.2\%$ at 36.4° C. The curves intersect at 12% and 35.8° C., a very close agreement of observed and fitted values. The isocontours of all four resonances should in principle intersect at the same value of $pO_2$ and temperature. In practice each pair of lines intersects at a slightly different value due to experimental errors.

Figure 20:
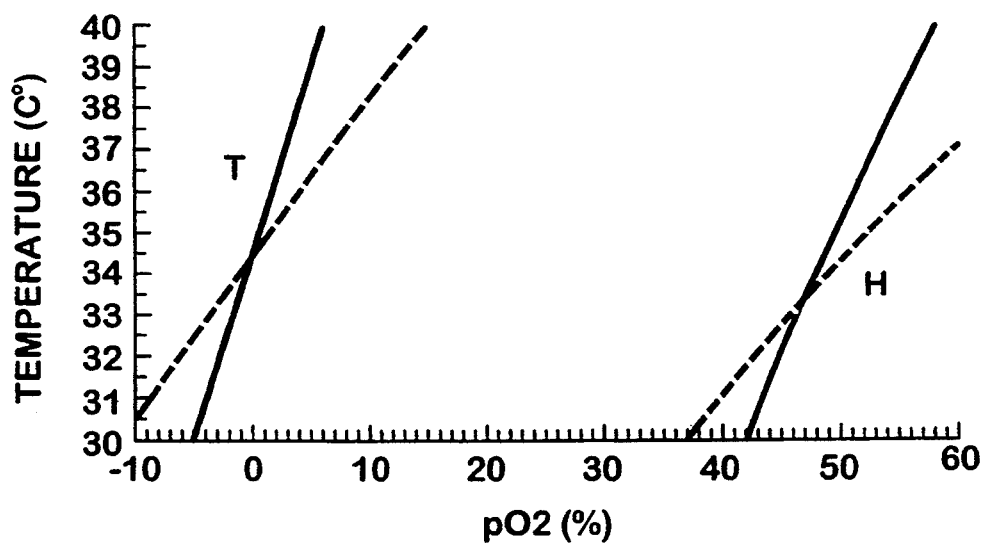
FIG. 20 shows the simultaneous determination of temperature and pO$_2$ in vivo in a murine tumor and a perfused rat heart.

FIG. 20 shows the simultaneous determination of temperature and $pO_2$ in vivo in the murine tumor (T, left) and the perfused rat heart (H, right). In each case $R_1$ isocontours are shown for $CF_3$ (solid) and $\beta\text{-}CF_2$ (dotted) resonances with the intersection defining $pO_2$ and temperature. In the tumor $R_1$ ($CF_3$) = 0.921 ± 0.025 s$^{-1}$, and $R_1$ ($CF_2$) = 1.876 ± 0.06 s$^{-1}$, giving $pO_2 = 0\%$ (0 Torr) at 34.6° C. In the heart $R_1$ ($CF_3$) = 1.898 ± 0.050 s$^{-1}$, and $R_1$ ($CF_2$) = 2.755 ± 0.15 s$^{-1}$, giving $pO_2 = 47.9\%$ (360 Torr) at 33.7° C.

Figure 21:
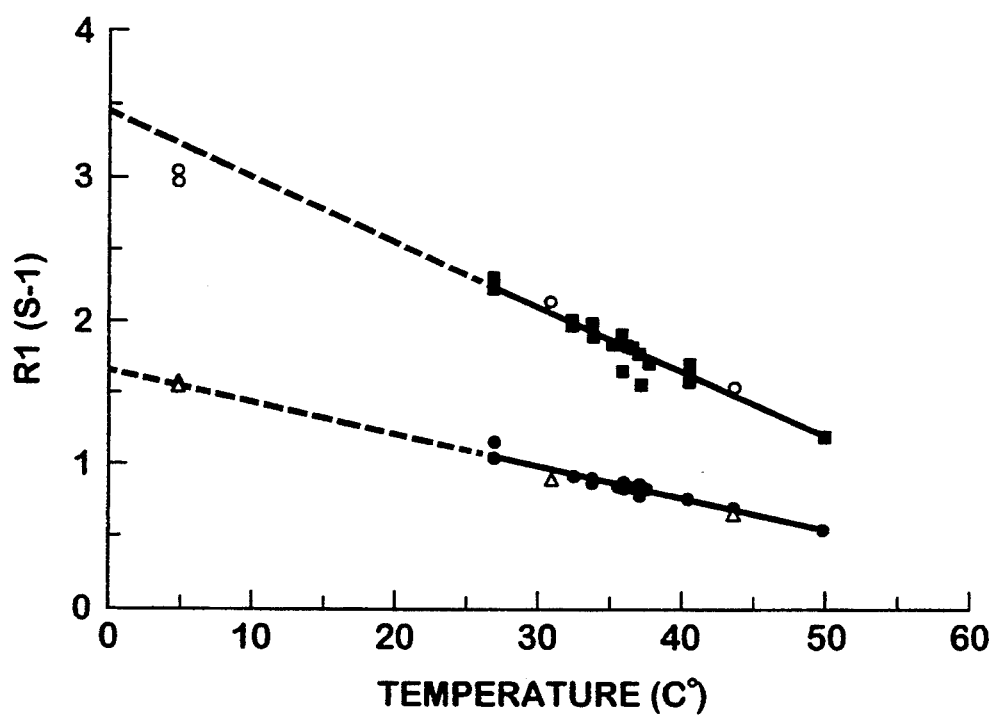
FIG. 21 shows the effect of tissue sequestration of the $^{19}$F R$_1$ of Oxypherol.

FIG. 21 shows the effect of tissue sequestration on $^{19}F$ $R_1$ of Oxypherol. $R_1$ in solution ($pO_2 = 0\%$): ● $CF_3$, ■ $\beta\text{-}CF_2$; $R_1$ in excised hypoxic liver: △ $CF_3$ ◯ $\beta\text{-}CF_2$. At 31° C. and 44° C., $R_1$ is equivalent in tissue or solution, validating the use of this technique to measure temperatures in vivo.

Figure 22:
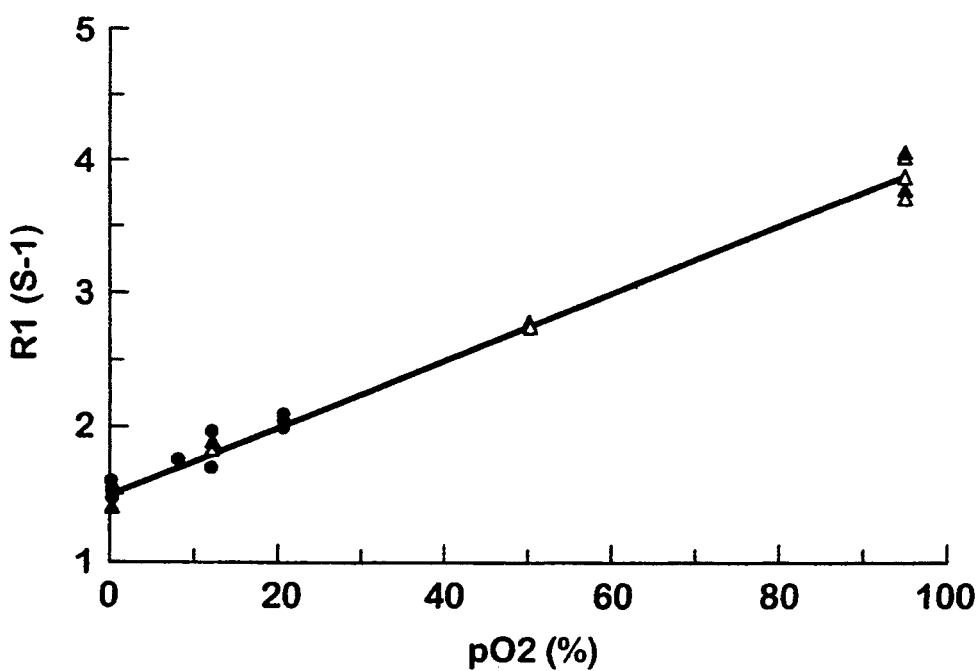
FIG. 22 shows the response of $^{19}$F R$_1$ of the CF$_3$ resonance of Oxypherol to variations in pO$_2$ at 5° C.

FIG. 22 shows the response of $^{19}F$ $R_1$ of the $CF_3$ resonance of Oxypherol to variations in $pO_2$ at 5° C. ● solution; △ KCl arrested Langendorff perfused rat heart). $AVO_2$ difference = 0% using oxygen electrodes. This validates the use of $^{19}F$ $R_1$ of Oxypherol to monitor $pO_2$ in vivo.

A composition in accordance with the present invention is preferably administered to a living subject parenterally, and most preferably intravenously. Preferred dosages are believed to be between 0.1–1.0 ml/kg body weight. The administration of multiple doses of PFC emulsion enhances the concentration of PFC and thus, tissues which tend to accumulate little PFC, such as tumors and the heart, can be more efficiently observed.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A method of non-invasively determining oxygen tension and temperature of tissue in a living mammalian subject, including the steps of:

administering to a living mammalian subject a biologically compatible $^{19}$F-containing spectroscopy agent in an amount effective to generate a measurable $^{19}$F spectrum under $^{19}$F NMR spectroscopy, wherein the $^{19}$F-containing spectroscopy agent has at least two $^{19}$F resonances which can be detected simultaneously by $^{19}$F NMR spectroscopy;

allowing sufficient time to elapse for substantially all of the $^{19}$F-containing spectroscopy agent to be cleared from the vascular system of the subject, with at least a portion of the $^{19}$F-containing spectroscopy agent becoming sequestered in tissue of the subject;

subjecting tissue in which the $^{19}$F-containing spectroscopy agent has become sequestered to a $^{19}$F magnetic resonance spectroscopy procedure, in which simultaneous measurements are made of spin-lattice relaxation rates from the at least two $^{19}$F resonances of the $^{19}$F-containing spectroscopy agent; and comparing the at least two spin-lattice relaxation rates measured in the $^{19}$F magnetic resonance spectroscopy procedure to a predetermined relation of spin-lattice relaxation rate to oxygen tension and temperature for the $^{19}$F-containing spectroscopy agent used at the magnetic field used, and thereby simultaneously determining the oxygen tension and temperature of the tissue.

2. The method of claim 1, where the oxygen tension is determined by a graphical comparison of the at least two independent measurements of spin-lattice relaxation rates with the predetermined relation of spin-lattice relaxation rate to oxygen tension.

3. The method of claim 1, where the oxygen tension is determined by solving simultaneous equations which are based on the predetermined relation of spin-lattice relaxation rate to oxygen tension, making use of the at least two spin-lattice relaxation rates measured.

4. The method of claim 1, where the $^{19}$F magnetic resonance spectroscopy procedure is a pulse-burst saturation recovery spectroscopy procedure.

5. The method of claim 1, where the $^{19}$F-containing spectroscopy agent contains a perfluorocarbon emulsion.

6. The method of claim 1, where neither oxygen tension nor temperature of the tissue is directly measured.

7. A method of non-invasively determining oxygen tension and temperature of tissue in a living mammalian subject, including the steps of:

administering to a living mammalian subject a biologically compatible perfluorocarbon emulsion which has at least two $^{19}$F resonances which can be detected simultaneously, in an amount effective to generate a measurable $^{19}$F spectrum under $^{19}$F NMR spectroscopy;

allowing sufficient time to elapse for substantially all of the perfluorocarbon emulsion to be cleared from the vascular system of the subject, with at least a portion of the perfluorocarbon emulsion becoming sequestered in tissue of the subject;

subjecting tissue in which the perfluorocarbon emulsion has become sequestered to a $^{19}$F magnetic resonance spectroscopy procedure in which simultaneous measurements are made of spin-lattice relaxation rates for the at least two $^{19}$F resonances of the perfluorocarbon emulsion; and comparing the at least two spin-lattice relaxation rates measured in the $^{19}$F magnetic resonance spectroscopy procedure to a predetermined relation of spin-lattice relaxation rate to oxygen tension and temperature for the perfluorocarbon emulsion used at the magnetic field used, and thereby determining the oxygen tension and temperature of the tissue without directly measuring either.

* * * * *